US009453044B2

(12) United States Patent
Liu et al.

(10) Patent No.: US 9,453,044 B2
(45) Date of Patent: Sep. 27, 2016

(54) METHOD OF SYNTHESIZING PEPTIDES, PROTEINS AND BIOCONJUGATES

(71) Applicant: NANYANG TECHNOLOGICAL UNIVERSITY, Singapore (SG)

(72) Inventors: Chuan Fa Liu, Singapore (SG); Junfeng Zhao, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 14/376,675

(22) PCT Filed: Feb. 6, 2013

(86) PCT No.: PCT/SG2013/000052
§ 371 (c)(1),
(2) Date: Aug. 5, 2014

(87) PCT Pub. No.: WO2013/119184
PCT Pub. Date: Aug. 15, 2013

(65) Prior Publication Data
US 2015/0344519 A1    Dec. 3, 2015

Related U.S. Application Data

(60) Provisional application No. 61/595,853, filed on Feb. 7, 2012.

(51) Int. Cl.
| | |
|---|---|
| *C07K 1/10* | (2006.01) |
| *C07K 7/64* | (2006.01) |
| *C07K 1/02* | (2006.01) |
| *C07K 1/04* | (2006.01) |

(52) U.S. Cl.
CPC . *C07K 1/10* (2013.01); *C07K 1/02* (2013.01); *C07K 1/026* (2013.01); *C07K 1/04* (2013.01); *C07K 7/64* (2013.01)

(58) Field of Classification Search
CPC ..................................................... C07K 1/10
See application file for complete search history.

(56) References Cited

FOREIGN PATENT DOCUMENTS

WO        2011/017837 A1    2/2011

OTHER PUBLICATIONS

Bode et al., "Chemoselective Amide Ligations by Decarboxylative Condensations of N-Alkylhydroxylamines and α-Ketoacids" *Angew. Chem. Int. Ed.* 45:1248-1252 (2006).
Carpino et al., "Regioselective Removal of Allylic Nitro Groups via Hydride Transfer," *J. Org. Chem.* 51:3734-3736 (1986).
Cicchi et al., "1,3-Aminoalcohols by Reductive Cleavage of Isoxazolidines with Molybdenum Hexacarbonyl," *Tetrahedron Letters* 31(23):3351-3354 (1990).
Dawson et al., "Synthesis of Proteins by Native Chemical Ligation," *Science, New Series* 266(5186):776-779 (Nov. 4, 1994).
Dawson et al., "Synthesis of Native Proteins by Chemical Ligation," *Annu. Rev. Biochem* 69:923-960 (2000).
Gravestock et al., "Retro-Cope Eliminations in the Synthesis of 1,2,5-Oxadiazinanes from Allylamines and Nitrones: a Method for the Amination of Unactivated Alkenes," *J. Chem. Soc., Chem. Commun.* 169-171 (1993).
Grundke et al., Optically Active N-Hydroxy-x-1-Amino Acid Methyl Esters: An Improved and Simplified Synthesis:*Communications, Synthesis* pp. 1115-1116 (Dec. 1987).
Hackenberger et al., "Chemoselective Ligation and Modification Strategies for Peptides and Proteins," *Angew. Chem. Int. Ed.* 47:10030-10074 (2008).
Hahn et al., "Manipulating proteins with chemistry: a cross-section of chemical biology," *Trends in Biochemical Sciences* 30(1):26-34 (Jan. 2005).
Koizumi et al., "High Asymmetric Induction in the 1,3-Dipolar Cycloaddition of (R)-(+)-p-Tolyl Vinyl Sulfoxide with Acyclic Nitrones," *J. Org. Chem.* 47:4004-4005 (1982).
Li et al., "Salicylaldehyde Ester-Induced Chemoselective Peptide Ligations: Enabling Generation of Natural Peptidic Linkages at the Serine/Threonine Sites," *Organic Letters* 12(8):1724-1727 (2010).
Liu et al., "Chemical Ligation Approach to Form a Peptide Bond between Unprotected Peptide Segments. Concept and Model Study," *Journal of the American Chemical Society* 116(10):4149-4153 (May 18, 1994).
Liu et al., "Peptide segment ligation strategy without use of protecting groups," *Proc. Natl. Acad. Sci. USA* 91:6584-6588 (Jul. 1994).
Liu et al., "Acyl Disulfide-Mediated Intramolecular Acylation for Orthogonal Coupling Between Unprotected Peptide Segments, Mechanism and Application," *Tetrahedron Letters* 37(7):933-936 (1996).
Mattingly et al., "Titanium Trichloride Reduction of Substituted N-Hydroxy-2-azetidinones and Other Hydroxamic Acids," *J. Org. Chem.* 45:410-415 (1980).
McAuley et al., "An Unusual Samarium Diiodide Mediated Reductive Ring Contraction of a Tricyclic Oxazine to a Highly-Functionalized Cyclopentane and Cyclobutane," *Organic Letters* 2(10):1457-1459 (2000).
Miller et al., "Synthesis of β-Lactams from Substituted Hydroxamic Acids," *J. Am. Chem. Soc.* 102:7026-7032 (1980).
Merrifield, "Solid Phase Peptide Synthesis. I. The Synthesis of a Tetrapeptide," 85:2149-2154 (Jan. 31, 1963).

(Continued)

*Primary Examiner* — Amber D Steele
(74) *Attorney, Agent, or Firm* — Seed IP Law Group PLLC

(57) ABSTRACT

The invention relates to the synthesis of peptides, proteins and related bioconjugates, and in particular, to such synthesis using a peptide ligation method whereby a C-terminal salicylaldehyde ester peptide is reacted with an aminoacyl-N-hydroxl peptide. The invention also relates to the synthesis of cyclic peptides, including serinyl- or threonyl-containing cyclic peptides. The invention further relates to a solid phase synthesis of C-terminal salicylaldehyde ester peptides.

20 Claims, No Drawings

(56) References Cited

OTHER PUBLICATIONS

Sheldrake et al., "Selective Opening of Ring C in the Morphine Skelton by an Unexpected Cleavage of the C5—C6 Bond in Cycloadducts of Thebaine and Acyl Nitroso Compounds," *J. Org. Chem.* 71:789-791 (2006).

Soellner et al., "Reaction Mechanism and Kinetics of the Traceless Staudinger Ligation," *J. Am. Chem. Soc.* 128:8820-8828 (2006).

Tam et al., "Peptide synthesis using unprotected peptides through orthogonal coupling methods," *Proc. Natl. Acad. Sci. USA* 92:12485-12489 (Dec. 1995).

Tam et al., "Stereospecific Pseudoproline Ligation of N-Terminal Serine, Threonine, or Cysteine-Containing Unprotected Peptides," *J. Am. Chem. Soc.* 121:9013-9022 (1999).

Tam et al., "Orthogonal Ligation Strategies for Peptide and Protein," *Biopolymers (Peptide Science)* 51:311-332 (1999).

Tam et al., "Chemical Synthesis of Circular Proteins," *Journal of Biological Chemistry* 287(32):27020-27025 (Aug. 3, 2012).

Wovkulich et al., "A Chiral Synthesis of L-Acosamine and L-Daunosamine via an Enantioselective Intramolecular [3+2] Cycloaddition," *J. Am. Chem. Soc.* 103:3956-3958 (1981).

Wu et al., "β-Scission of the N—O Bond in Alkyl Hydroxamate Radicals: A Fast Radical Trap," *Organic Letters* 2(10): 1345-1348 (2000).

METHOD OF SYNTHESIZING PEPTIDES, PROTEINS AND BIOCONJUGATES

CROSS-REFERENCE TO RELATED APPLICATION

This application claims the benefit of priority of U.S. Provisional Patent Application No. 61/595,853, filed Feb. 7, 2012, the contents of which being hereby incorporated by reference in its entirety for all purposes.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_461USPC_SEQUENCE_LISTING.txt. The text file is 4.6 KB, was created on Jun. 6, 2015, and is being submitted electronically via EFS-Web.

TECHNICAL FIELD

The invention relates to the synthesis of peptides, proteins and related bioconjugates, and in particular, to such synthesis using a peptide ligation method whereby a C-terminal salicylaldehyde ester peptide is reacted with an aminoacyl-N-hydroxl peptide. The invention also relates to the synthesis of cyclic peptides, including serinyl- or threonyl-containing cyclic peptides. The invention further relates to a solid phase synthesis of C-terminal salicylaldehyde ester peptides.

BACKGROUND

As biofunctional molecules, peptides and proteins are used ubiquitously as essential reagents in basic life science research. More importantly, many bioactive peptides and proteins also have direct therapeutic value. In fact, peptide- and protein-based biologics are a mainstay therapeutic modality of modern day pharmaceutical industry, and about 40% of all experimental drugs currently under the various stages of clinical development are peptides and proteins, or their bioconjugates. Therefore, methods that allow for efficient synthesis of these biomolecules not only can provide important enabling technologies for basic biomedical research, but also for drug discovery.

Traditionally, solid phase peptide synthesis (SPPS) is the method of choice for preparing small to medium-sized peptides. Since its discovery, SPPS has been a choice of use in the synthesis of countless peptides. As an advantage to the chemical synthesis, peptides synthesized by SPPS may contain any kinds of structural units, such as D-amino acids and other non-natural amino acids, and/or have some unusual architectures. However, for practical reasons, it is technically very challenging to use SPPS for synthesizing very large peptides or proteins. Recombinant DNA technology is the classic method for protein production. However, this technology suffers from several limitations, such as inability to produce unnatural or post-translationally modified proteins, difficulty in expressing multi-domain proteins or proteins that are toxic to the host cell, and problems of product heterogeneity due to uncontrolled processing of nascent polypeptide chains.

A significant advance in chemical biology for the past two decades has been the development of chemoselective peptide ligation methods for protein synthesis. With these advance methods, one can use peptides and protein domains produced by SPPS and recombinant DNA technology as building blocks for the construction of large, complex protein molecules, therefore overcoming the limitations of existing technologies. As a common feature, almost all the currently available ligation chemistry is characterized by a typical two-step reaction scheme: a prior capture step to bring together the reacting C- and N-termini of two peptide components, followed by an intra-molecular reaction for peptide bond formation.

For many of these ligation methods, the capture reaction usually involves a side-chain functional group on the N-terminal amino acid of the second peptide component. For instance, the unique soft nucleophilicity of the thiol group has been exploited as the capture device in the development of the thioester-cysteine ligation method (also known as native chemical ligation) whereby the capture step is a transthioesterification reaction between a C-terminal thioester of the first peptide and the N-terminal cysteine (Cys) thiol group of the second peptide. This ligation method has also been extended to non-Cys residues through introducing a temporary thiol group onto their side chains. Similarly, the thioacid capture ligation method is so-named because a super-nucleophilic C-terminal thioacid of the first peptide can be captured very efficiently by the Npys-activated thiol of the N-terminal Cys residue of the second peptide. The 1,2-aminoethanethiol of N-terminal Cys and 1,2-aminoethanol moiety of an N-terminal Ser/Thr residue have also been used to develop the so-called aldehyde capture ligation methods. In fact, the glycoaldehyde ester-mediated ligation is the earliest peptide ligation method developed, in which a highly selective thiazolidine/oxazolidine formation reaction serves as the capture reaction which is followed by an S- or O-to-N acyl transfer step to form a pseudoproline residue at the ligation site.

Recently, a C-terminal salicylaldehyde ester is used to replace the glycoaldehyde ester to give a highly efficient ligation reaction after which the salicylaldehyde moiety can be readily removed in an acidolysis reaction to generate native Ser or Thr at the ligation junction. This development is significant in that it is one of the rare methods that does not depend on a thiol group for the ligation reaction and that Ser or Thr is much more abundant than Cys in natural proteins. Other ligation methods that do not depend on a sidechain thiol or any sidechain functionality include the Staudinger ligation and the decarboxylative condensation method. However, these two methods have limited practical utility because of the low efficiency of the ligation reaction.

As seen from above, so far all the existing methods require a side-chain functional group on the N-terminal aminoacid residue of the second peptide to mediate the ligation reaction, which limits the application scope of these methods.

SUMMARY

A peptide ligation method useful for protein synthesis is described herein. The method for the peptide ligation does not involve a side-chain group. Advantageously, the method allows for ligation at virtually any peptide bond junctions. The method relates to an aldehyde capture reaction involving a C-terminal salicylaldehyde ester of one peptide with an aminoacyl-N-hydroxl peptide of another peptide. Subsequent O-to-N acyl transfer and removal of the auxiliary salicylaldehye and N-hydroxy moieties generate a natural peptide bond at the ligation junction. A method for the preparation of peptide C-terminal salicylaldehyde esters to provide the building blocks for this ligation scheme as well as for cyclic peptide synthesis is also disclosed herein.

Thus, according to a first aspect, there is provided a method of preparing a polypeptide or protein of formula (3)

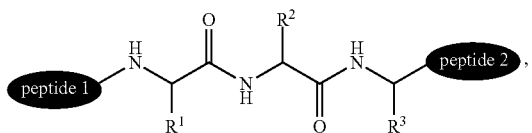

(3)

comprising reacting a C-terminal salicylaldehyde ester peptide of formula (1)

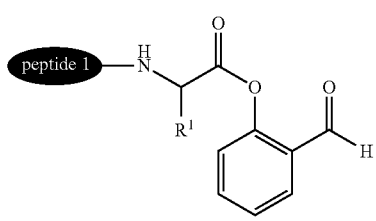

(1)

with an aminoacyl-N-hydroxyl peptide of formula (2)

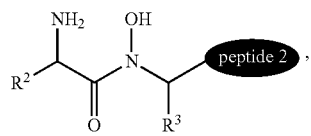

(2)

wherein the reaction is carried out in a pyridine/organic acid mixture to form an intermediate compound having a 1,2,5-oxadiazinane ring structure; and adding a reducing agent to cleave the 1,2,5-oxadiazinane ring structure of the intermediate compound to form the polypeptide or protein of formula (3), wherein each of $R^1$, $R^2$ and $R^3$ is independently selected from the group consisting of H, a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl, and a side chain of an amino acid; or $R^1$ is $C_1$-$C_{10}$ alkylyl that forms together with the nitrogen of the adjacent backbone imino group, a heteroalicyclic ring.

The intermediate compound has the following formula (4):

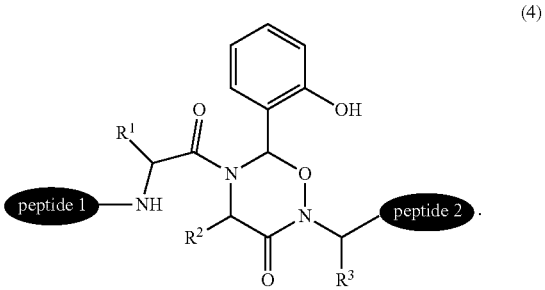

(4)

In various embodiments, at least one of $R^1$, $R^2$ and $R^3$ is independently a side chain of an amino acid.

In further various embodiments, at least one of $R^1$ and $R^3$ is independently selected from the group consisting of H, $CH_3$, $CH(CH_3)_2$, $CH_2CH(CH_3)_2$, $CH(CH_3)CH_2CH_3$, $(CH_2)_2$—S—$CH_3$, $CH_2$—SH, $CH_2$—OH, $CHOH$—$CH_3$, $CH_2$-(3-indolyl), $CH_2$-phenyl, $(CH_2)_4$—$NH_2$, $(CH_2)_3$—NH—C(=NH)$NH_2$, $CH_2$-1H-imidazol-4-yl, $CH_2$-(p-hydroxy-phenyl), $CH_2$—C(O)$NH_2$, $(CH_2)_2$—C(O)$NH_2$, $CH_2$—COOH, and $(CH_2)_2$—COOH, or $R^1$ is $(CH_2)_3$ that forms together with the nitrogen of the adjacent backbone imino group a 5-membered heteroalicyclic ring.

In further various embodiments, $R^2$ is selected from the group consisting of H, $CH_3$, $CH(CH_3)_2$, $CH_2CH(CH_3)_2$, $CH(CH_3)CH_2CH_3$, $(CH_2)_2$—S—$CH_3$, $CH_2$—SH, $CH_2$—OH, $CHOH$—$CH_3$, $CH_2$-(3-indolyl), $CH_2$-phenyl, $(CH_2)_4$—$NH_2$, $(CH_2)_3$—NH—C(=NH)$NH_2$, $CH_2$-1H-imidazol-4-yl, $CH_2$-(p-hydroxy-phenyl), $CH_2$—C(O)$NH_2$, $(CH_2)_2$—C(O)$NH_2$, $CH_2$—COOH, and $(CH_2)_2$—COOH. In yet further various embodiments, in cases where $R^2$ is $CH_2$—SH, $CH_2$—OH or $CHOH$—$CH_3$, the thiol or hydroxyl side-chain is protected with a protecting group.

In certain embodiments, at least one of $R^1$, $R^2$ and $R^3$ is independently selected from the group consisting of $CH_3$, $CH_2$-phenyl, $CH_2CH(CH_3)_2$, $CH(CH_3)_2$ and H.

In one embodiment, the reducing agent is samarium (II) iodide ($SmI_2$) solution.

A second aspect relates to a method of preparing a cyclic peptide of formula (5)

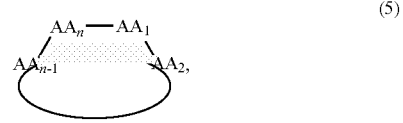

(5)

where $AA_n$ represents an amino acid at a $n^{th}$ position of the peptide,
comprising:
reacting the C-terminal salicylaldehyde ester peptide of formula (1A)

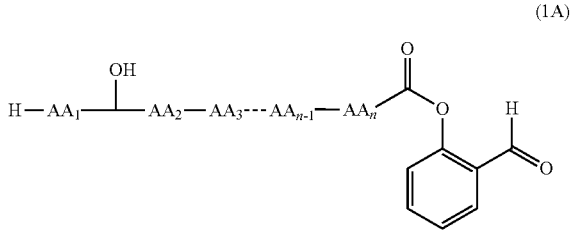

(1A)

in a pyridine/organic acid mixture, where " - - - " represents additional amino acids in the chain of the peptide; and adding a reducing agent to form the cyclic peptide of formula (5).

In a third aspect, there is disclosed a method of preparing a serinyl- or threonyl-containing cyclic peptide of formula (6)

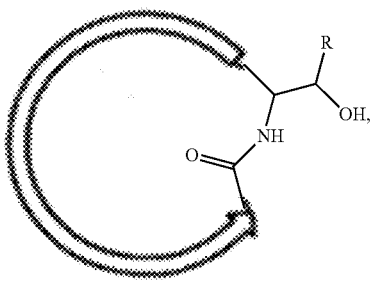

(6)

where the peptide contains serine (Ser) or threonine (Thr), comprising:
reacting the C-terminal Ser- or Thr-containing salicylaldehyde ester peptide of formula (1B)

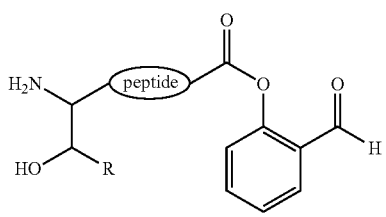

(1B)

in a pyridine/organic acid mixture; and
adding an acidic deprotecting agent to form the serinyl- or threonyl-containing cyclic peptide of formula (6),
wherein R is a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl, or a side chain of an amino acid.

According to a fourth aspect, a method of preparing a C-terminal salicylaldehyde ester peptide in solid phase is disclosed. The method comprises:
(i) mixing 2-hydroxycinnamic acid and 4-methylbenzhydrylamine hydrochloride salt (MBHA) resin in the presence of benzotriazol-1-yl-oxytripyrrolidinophosphonium hexafluorophosphate (PyBOP) and a tertiary amine to form a 2-hydroxycinnamide linker on the resin;
(ii) coupling a Boc-amino acid to the 2-hydroxycinnamide-resin, followed by a standard Boc solid phase peptide synthesis to form a peptidyl 2-hydroxycinnamide phenolic ester on the resin, where Boc represents tert-butoxycarbonyl protecting group;
(iii) adding a cleavage agent such as hydrofluoric acid or trifluoromethanesulfonic acid—trifluoroacetic acid mixture to release the peptidyl 2-hydroxycinnamide phenolic ester from the resin; and
(iv) ozonizing the C=C bond of the peptidyl 2-hydroxycinnamamide phenolic ester to obtain the C-terminal salicylaldehyde ester peptide.

In a fifth aspect, there is provided a method of preparing a polypeptide or protein of formula (7)

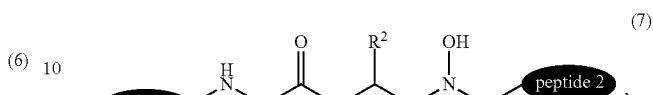

(7)

comprising reacting a compound of formula (4)

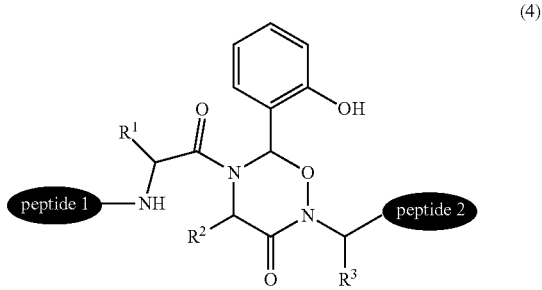

(4)

with trifluoroacetic acid (TFA),
wherein each of $R^1$, $R^2$ and $R^3$ is independently selected from the group consisting of H, a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl, and a side chain of an amino acid.

DESCRIPTION

The following detailed description refers to the accompanying drawings that show, by way of illustration, specific details and embodiments in which the invention may be practised. These embodiments are described in sufficient detail to enable those skilled in the art to practise the invention. Other embodiments may be utilized and changes may be made without departing from the scope of the invention. The various embodiments are not necessarily mutually exclusive, as some embodiments can be combined with one or more other embodiments to form new embodiments.

Scheme 1 below outlines the present design rationales of an aldehyde-capture ligation method between two peptides ("peptide 1" and "peptide 2") that does not rely on a side-chain functional group. An N-hydroxyl group is introduced onto a first peptide bond of a second ligation partner ("peptide 2"), i.e. the amide linkage between the N-terminal amino acid and the second amino acid residue. This N-hydroxyl group, together with the N-terminal amine, form a 1,3-disubstituted moiety that fulfils the requirement of a capture group for an aldehyde group since a capture reaction between the two leads to the formation of a relatively stable intermediate compound having a 1,2,5-oxadiazinane ring structure. The following O-to-N acyl transfer reaction forms an amide bond between the two ligation peptides partners. Lastly, a native peptide bond is generated at the ligation junction after the six-membered ring structure is cleaved in a suitable reaction. As can be seen in Scheme 1, the first ligation peptide has a C-terminal salicylaldehyde ester, the use of which not only facilitates the O-to-N acyl shift reaction but advantageously also its self removal from the ligation product.

hyde, (2) oxidizing the Schiff's base with 3-chloroperoxybenzoic acid to give an oxaziridine product and (3) cleaving the oxaziridine ring with hydroxylamine hydrochloride to afford N-hydroxy-α-L-amino acid t-butyl ester. When the ligation reaction was tested in the model system, it was interesting to note that the 1,2,5-oxadiazinane 3 with a six-membered cyclic N,O-benzylidene acetal and a new peptide bond was formed readily in 2 h after mixing Fmoc-alanyl salicylaldehyde ester 1 and N-hydroxy dipeptide 2 in Scheme 1. Illustration of Present Aldehyde-Capture Ligation Scheme.

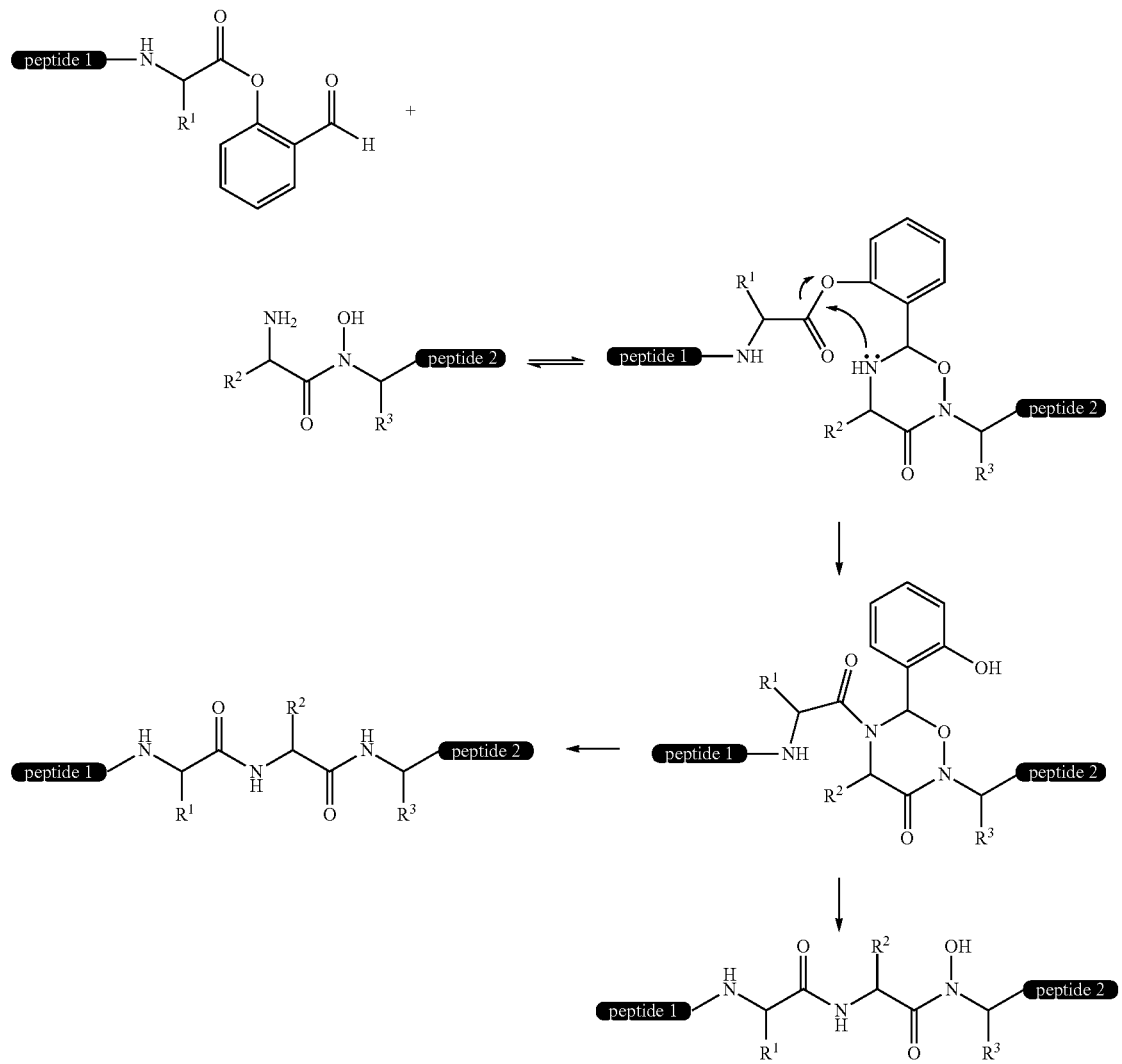

The feasibility of presently disclosed ligation scheme is demonstrated in a small model system (Scheme 2). Fmoc-alanyl salicylaldehyde ester 1 was prepared from Fmoc-Ala-OH and salicylaldehyde using DCC. The amine component N-hydroxy dipeptide 2 was prepared according to literature procedures (Grunduke et al, Synthesis, 1987, 1115-1116; Carpino et al, J. Org. Chem. 1986, 51:3734-3736). Briefly, 2 was prepared by coupling an Fmoc amino acid chloride to an N-hydroxy-α-L-amino acid t-butyl ester in dichloromethane in the presence of $NaHCO_3$, followed by removal of Fmoc. The N-hydroxy-α-L-amino acid t-butyl ester was synthesized in three steps: (1) preparing a Schiff's base of the α-L-amino acid t-butyl ester with 4-methoxybenzaldehyde, pyridine/acetic acid (1/1 mol/mol). After evaporation of the solvent, 3 was isolated as a mixture of four isomers one pair of which due to the acetal chiral center and the other pair due to cis and trans conformations of the newly formed amide bond. The removal of the acetal group in an acidic cocktail solution ($TFA/H_2O/i-Pr_3SiH$) gave the N-hydroxy tripeptide 4 in excellent yield. However, a problem was encountered in removing the N-hydroxyl in tripeptide 4 to convert it to the natural tripeptide 5. Part of the newly formed peptide bond was hydrolyzed in acidic aqueous condition employed for the reduction of N-hydroxy group. This might be partially attributed to the fact that the N-hydroxyl group contributed to the neighboring group-assisted hydrolysis of the peptide bond. The present inventors therefore hypothesized that this problem would be avoided if the N—O bond was cleaved before the deprotection of the cyclic acetal structure in 3.

In attempting to solve this problem, the present inventors conducted a series of tests to screen for suitable reducing agents. After screening a number of reducing agents for the cleavage of N—O bond, it was surprisingly found that samarium (II) iodide (SmI$_2$) was the best reducing agent that fulfilled the above requirement. In this respect, SmI$_2$ treatment was unexpectedly found that in addition to cleaving the N—O bond, it advantageously cleaved the benzylic N—C bond to give the natural peptide 5 directly. In one embodiment, the tripeptide 5 was obtained in high yield when the mixture of the four isomers of 3 was treated with 0.1 M SmI$_2$ solution in tetrahyfuran (THF) at room temperature. In addition, SmI$_2$ can be used in the presence of water or trifluoroethanol (TFE) which helps to dissolve peptides.

comprising reacting a C-terminal salicylaldehyde ester peptide of formula (1)

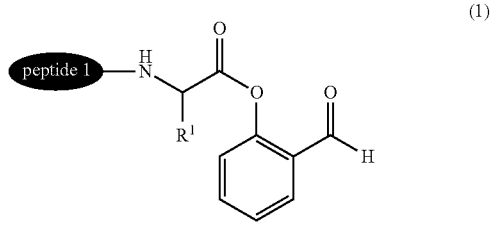

with an aminoacyl-N-hydroxyl peptide of formula (2)

Scheme 2. Optimization of the Present Two-Step Peptide Ligation Scheme

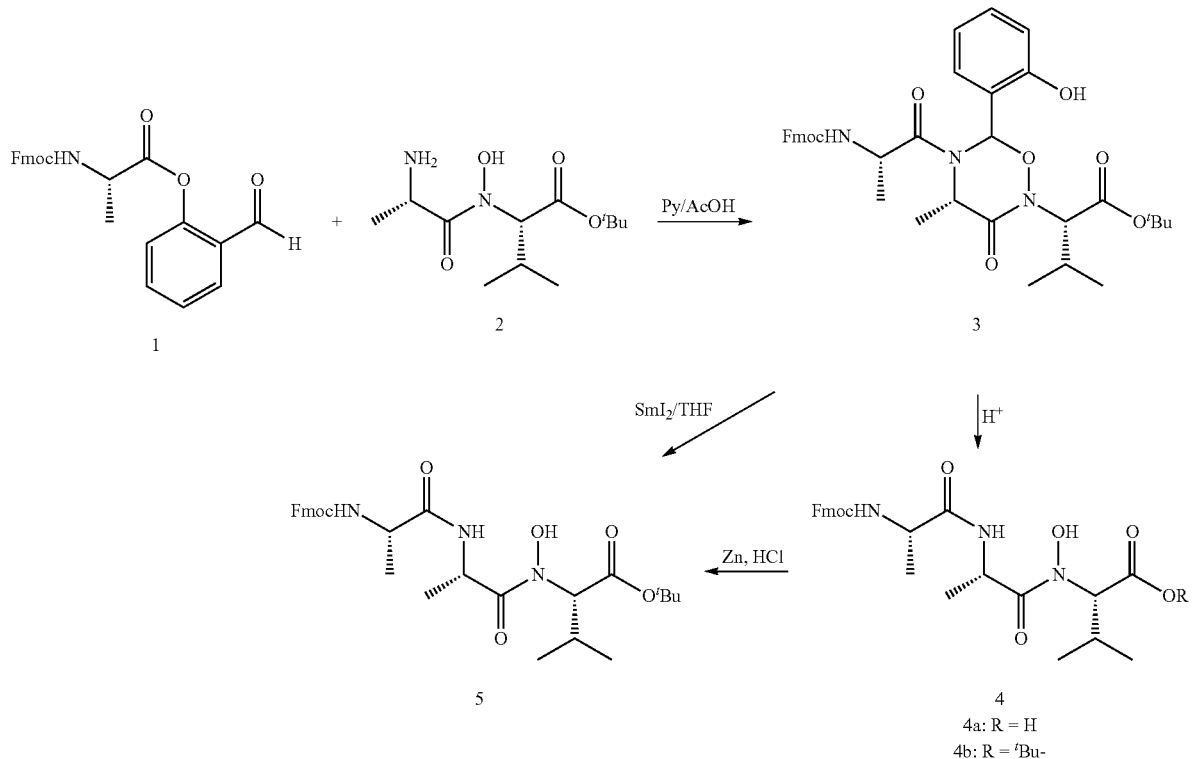

Thus, according to a first aspect of present disclosure, there is provided a method of preparing a polypeptide or protein of formula (3)

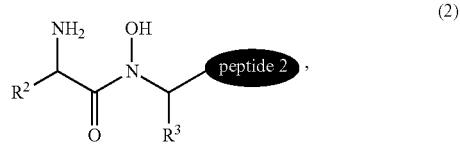

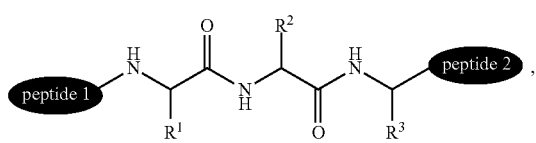

wherein the reaction is carried out in a pyridine/organic acid mixture to form an intermediate compound having a 1,2,5-oxadiazinane ring structure; and adding a reducing agent to cleave the 1,2,5-oxadiazinane ring structure of the intermediate compound to form the polypeptide or protein of formula (3), wherein each of R$^1$, R$^2$ and R$^3$ is independently selected from the group consisting of H, a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl, and a side chain of an amino acid; or $R^1$ is $C_1$-$C_{10}$ alkylyl that forms together with the nitrogen of the adjacent backbone imino group, a heteroalicyclic ring.

In one embodiment, the intermediate compound has the following formula (4):

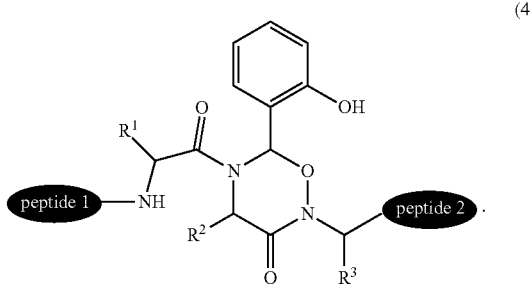

(4)

As used herein, a "peptide" generally has from about 3 to about 100 amino acids, whereas a polypeptide or protein has about 100 or more amino acids, up to a full length sequence translated from a gene. Additionally, as used herein, a peptide can be a subsequence or a portion of a polypeptide or protein. In certain embodiments the peptide consists of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues.

As used herein, an "amino acid residue" refers to any naturally or non-naturally occurring amino acid, any amino acid derivative or any amino acid mimic known in the art. Included are the L- as well as the D-forms of the respective amino acids, although the L forms are usually preferred. In various embodiments, the term relates to the 20 naturally occurring amino acids glycine (Gly), alanine (Ala), valine (Val), leucin (Leu), isoleucin (Ile), proline (Pro), cysteine (Cys), methionine (Met), serine (Ser), threonine (Thr), glutamine (Gln), asparagine (Asn), glutamic acid (Glu), aspartic acid (Asp), lysine Lys), histidine (His), arginine (Arg), phenylalanine (Phe), trypthophane (Trp), and tyrosine (Tyr) in their L form. In various embodiments, the amino acid side-chain may be a side-chain of Gly, Ala, Val, Leu, Ile, Met, Cys, Ser, Thr, Trp, Phe, Lys, Arg, His, Tyr, Asn, Gln, Asp, Glu, or Pro. In this context, a "side chain of an amino acid" includes a protecting group-containing side chain of an amino acid. For example, the protecting group may include, but is not limited to, 9-fluorenylmethyl carbamate (Fmoc), t-butyl carbamate (Boc), benzyl carbamate, acetamide, or trifluoroacetamide (TFA).

In various embodiments, the peptide may be 10 to 50 amino acids in length. In other embodiments, the peptide may be 15 to 25 amino acids in length.

The reducing agent may be any suitable reducing agent that cleaves the N—O bond of the 1,2,5-oxadiazinane ring structure of the intermediate compound. Advantageously, the reducing agent simultaneously cleaves the benzylic C—N bond of the 1,2,5-oxadiazinane ring structure of the intermediate compound to form the protein of formula (3) directly. Thus, in one embodiment, the reducing agent is samarium (II) iodide ($SmI_2$) solution. For example, the reducing agent may be $SmI_2$ solution in tetrahydrofuran (THF) or $SmI_2$ solution in trifluoroethanol (TFE).

Alternatively, a first reducing agent is used to cleave the N—O bond while a second reducing agent is used to cleave the benzylic C—N bond of the 1,2,5-oxadiazinane ring structure of the intermediate compound.

The ligation reaction is carried out in a pyridine/organic acid mixture. For example, the mixture may be, but not limited to, a pyridine/acetic acid mixture, pyridine/propionic acid mixture, pyridine/isobutyric acid mixture, or pyridine/butyric acid mixture. In one embodiment, the ligation reaction is carried out in a pyridine/acetic acid mixture. In another embodiment, the ligation reaction is carried out in a pyridine/isobutyric acid mixture. The ratio of pyridine to organic acid in the mixture may be, but is not limited to, 2/1 to ⅓, such as 2/1, 3/2, 4/3, 1/1, ⅔, ½, or ⅓ mol/mol. In one embodiment, the reaction is carried out in a pyridine/acetic acid (1/1 mol/mol) mixture.

The term "aliphatic", alone or in combination, refers to a straight chain or branched chain hydrocarbon comprising at least one carbon atom. Aliphatics include alkyls, alkenyls, and alkynyls. In certain embodiments, aliphatics are optionally substituted, i.e. substituted or unsubstituted. Aliphatics include, but are not limited to, methyl, ethyl, propyl, isopropyl, butyl, isobutyl, tert-butyl, pentyl, hexyl, ethenyl, propenyl, butenyl, ethynyl, butynyl, propynyl, and the like, each of which may be optionally substituted. As used herein, aliphatic is not intended to include cyclic groups.

The term "optionally substituted" or "substituted or unsubstituted" refers to a group in which none, one, or more than one of the hydrogen atoms have been replaced with one or more groups such as, but are not limited to, alkyl, alkenyl, alkynyl, heteroalkyl, cycloalkyl, aryl, alkylaryl, hydroxyl or heteroaryl.

The term "alkyl", alone or in combination, refers to a fully saturated aliphatic hydrocarbon. In certain embodiments, alkyls are optionally substituted, i.e. substituted or unsubstituted. In certain embodiments, an alkyl comprises 1 to 10 carbon atoms, for example 2 to 8 carbon atoms, wherein (whenever it appears herein in any of the definitions given below) a numerical range, such as "1 to 10" or "$C_1$-$C_{10}$", refers to each integer in the given range, e.g. "$C_1$-$C_{10}$ alkyl" means that an alkyl group comprising only 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms. Examples of alkyl groups include, but are not limited to, methyl, ethyl, n-propyl, isopropyl, n-butyl, isobutyl, sec-butyl, tert-butyl, tert-amyl, pentyl, hexyl, heptyl, octyl and the like. In certain embodiments, one or more carbon atoms may be replaced by a heteroatom to form a heteroalkyl (see definition below).

The term "alkenyl", alone or in combination, refers to an aliphatic hydrocarbon having one or more carbon-carbon double-bonds, such as two or three carbon-carbon double-bonds. In certain embodiments, alkenyls are optionally substituted, i.e. substituted or unsubstituted. In certain embodiments, an alkenyl comprises 2 to 15 carbon atoms, for example 2 to 10 carbon atoms. "$C_2$-$C_{15}$ alkenyl" means that an alkenyl group comprising only 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, or 15 carbon atoms. Examples of alkenyls include, but are not limited to, ethenyl, propenyl, butenyl, 1,4-butadienyl, pentenyl, hexenyl, 4-methylhex-1-enyl, 4-ethyl-2-methylhex-1-enyl and the like. In certain embodiments, one or more carbon atoms may be replaced by a heteroatom to form a heteroalkenyl (see definition below).

The term "alkynyl", alone or in combination, refers to an aliphatic hydrocarbon having one or more carbon-carbon triple-bonds, such as two or three carbon-carbon triple-bonds. In certain embodiments, alkynyls are optionally substituted, i.e. substituted or unsubstituted. In certain embodiments, an alkynyl comprises 2 to 15 carbon atoms, for example 2 to 10 carbon atoms. "$C_2$-$C_{15}$ alkynyl" means that an alkynyl group comprising only 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, or 15 carbon atoms. Examples of alkynyls include, but are not limited to, ethynyl, propynyl, butynyl, and the like. In certain embodiments, one or more carbon atoms may be replaced by a heteroatom to form a heteroalkynyl (see definition below).

The term "aromatic" refers to a group comprising a covalently closed planar ring having a delocalized [pi]-electron system comprising 4 n+2 [pi] electrons, where n is an integer. Aromatic rings may be formed by five, six, seven, eight, nine, or more than nine atoms. Aromatics may be optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon atoms, and optionally carrying one or more substituents selected from an aryl, a heteroaryl, a cycloalkyl, a non-aromatic heterocycle, a halo, a hydroxy, an amino, a cyano, a nitro, an alkylamido, an acyl, a $C_1$-$C_6$ alkoxy, a $C_1$-$C_6$ alkyl, a $C_1$-$C_6$ hydroxyalkyl, a $C_1$-$C_6$ aminoalkyl, an alkylsulfenyl, an alkylsulfinyl, an alkylsulfonyl, an sulfamoyl, or a trifluoromethyl. In certain embodiments, an aromatic group is substituted at one or more of the para, meta, and/or ortho positions. Examples of aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl)phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

The term "aryl" refers to an aromatic ring wherein each of the atoms forming the ring is a carbon atom. Aryl rings may be formed by five, six, seven, eight, nine, or more than nine carbon atoms. Aryl groups may be optionally substituted.

The term "heteroaryl" refers to an aromatic heterocycle. Heteroaryl rings may be formed by three, four, five, six, seven, eight, nine, or more than nine atoms. Heteroaryls may be optionally substituted. Examples of heteroaryl groups include, but are not limited to, aromatic $C_3$-$C_8$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_1$-$C_6$ alkoxy, $C_1$-$C_6$ alkyl, $C_1$-$C_6$ hydroxyalkyl, $C_1$-$C_6$ aminoalkyl, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, or $C_1$-$C_6$ alkyl.

The term "non-aromatic ring" refers to a group comprising a covalently closed ring that is not aromatic.

The term "alicyclic" refers to a group comprising a non-aromatic ring wherein each of the atoms forming the ring is a carbon atom. Alicyclic groups may be formed by three, four, five, six, seven, eight, nine, or more than nine carbon atoms. In certain embodiments, alicyclics are optionally substituted, i.e. substituted or unsubstituted. In certain embodiments, an alicyclic comprises one or more unsaturated bonds, such as one, two or three carbon-carbon double-bonds. Alicyclics include cycloalkyls and cycloalkenyls. Examples of cycloalkyls include, but are not limited to, cyclopropane, cyclobutane, cyclopentane, cyclohexane, and cycloheptane. Examples of cycloalkenyls include, but are not limited to, cyclopentene, cyclopentadiene, cyclohexene, 1,3-cyclohexadiene, 1,4-cyclohexadiene, and cycloheptene.

The term "heteroatom" refers to an atom other than carbon or hydrogen. Heteroatoms are typically independently selected from oxygen, sulfur, nitrogen, and phosphorus, but are not limited to those atoms. In embodiments in which two or more heteroatoms are present, the two or more heteroatoms may all be the same as one another, or some or all of the two or more heteroatoms may each be different from the others.

The term "heteroaliphatic", alone or in combination, refers to a group comprising an aliphatic hydrocarbon (such as alkyl, alkenyl, and alkynyl) and one or more heteroatoms. In certain embodiments, heteroaliphatics are optionally substituted, i.e. substituted or unsubstituted. Certain heteroaliphatics are acylaliphatics, in which the one or more heteroatoms are not within an aliphatic chain. Heteroaliphatics include heteroalkyls, including, but not limited to, acylalkyls, heteroalkenyls, including, but not limited to, acylalkenyls, and heteroalkynyls, including, but not limited acylalkynyls. Examples of heteroaliphatics include, but are not limited to, $(CH_2)_2$—S—$CH_3$, $CH_2$—SH, $CH_3C(=O)CH_2$—, $CH_3C(=O)CH_2CH_2$—; $CH_3CH_2C(=O)CH_2CH_2$—, $CH_3C(=O)CH_2CH_2CH_2$—, $CH_3OCH_2CH_2$—, $CH_3NHCH_2$—, and the like.

The term "heterocycle" refers to a group comprising a covalently closed ring wherein at least one atom forming the ring is a carbon atom and at least one atom forming the ring is a heteroatom. Heterocyclic rings may be formed by three, four, five, six, seven, eight, nine, or more than nine atoms. Any number of those atoms may be heteroatoms (i.e., a heterocyclic ring may comprise one, two, three, four, five, six, seven, eight, nine, or more than nine heteroatoms). Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring will have additional heteroatoms in the ring. In heterocycles comprising two or more heteroatoms, those two or more heteroatoms may be the same or different from one another. Heterocycles may be optionally substituted. Binding to a heterocycle can be at a heteroatom or via a carbon atom. Examples of heterocycles include heterocycloalkyls (where the ring contains fully saturated bonds) and heterocycloalkenyls (where the ring contains one or more unsaturated bonds) such as, but are not limited to the following:

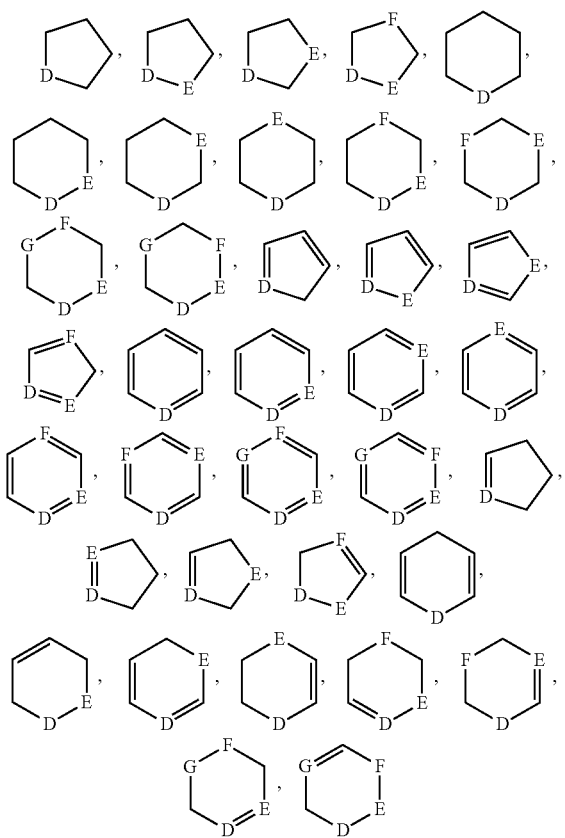

wherein D, E, F, and G independently represent a heteroatom. Each of D, E, F, and G may be the same or different from one another. In an illustrative embodiment, the heterocycle may be $CH_2$-1H-imidazol-4-yl, i.e. a side-chain of histidine amino acid.

The term "ring" refers to any covalently closed structure. Rings include, for example, carbocycles (e.g., aryls and alicyclics), heterocycles (e.g., heteroaryls and non-aromatic heterocycles), aromatics (e.g., aryls and heteroaryls), and non-aromatics (e.g., alicyclics and non-aromatic heterocycles). Rings may be optionally substituted.

The term "alkylaryl" refers to a group comprising an aryl group bound to an alkyl group.

In certain embodiments, at least one of $R^1$, $R^2$ or $R^3$ is an alkyl. The alkyl can be a primary alkyl, a secondary alkyl, or a tertiary alkyl. The alkyl can be substituted or unsubstituted. The alkyl can also include one or more heteroatoms in the main chain of the alkyl wherein one or more of the carbon atoms are replaced by the one or more heteroatom, i.e. a heteroalkyl. The alkyl can also form a ring, i.e. a cycloalkyl. The cycloalkyl can further include one or more heteroatoms in the ring wherein one or more of the carbon atoms in the ring are replaced by the one or more heteroatoms, i.e. a heterocycloalkyl. The alkyl can also be bound to an aryl to form an alkylaryl, such as a benzyl, or to a non-aromatic ring.

In other embodiments, at least one of $R^1$, $R^2$ or $R^3$ is an alkenyl. The alkenyl can have a cis- or trans-configuration. The alkenyl can be substituted or unsubstituted. The alkenyl can also include one or more heteroatoms in the main chain of the alkenyl wherein one or more of the carbon atoms are replaced by the one or more heteroatom, i.e. a heteroalkenyl. The alkenyl can also form a ring, i.e. a cycloalkenyl. The cycloalkenyl can further include one or more heteroatoms in the ring wherein one or more of the carbon atoms in the ring are replaced by the one or more heteroatoms, i.e. a heterocycloalkenyl. The alkenyl can also be bound to an aryl or to a non-aromatic ring.

In further embodiments, at least one of $R^1$, $R^2$ or $R^3$ is an alkynyl. The alkenyl can be substituted or unsubstituted. The alkynyl can also include one or more heteroatoms in the main chain of the alkynyl wherein one or more of the carbon atoms are replaced by the one or more heteroatom, i.e. a heteroalkynyl. The alkynyl can also be bound to an aryl or to a non-aromatic ring.

In yet further embodiments, at least one of $R^1$, $R^2$ or $R^3$ is an aryl or is aromatic. The aryl can be substituted or unsubstituted. The aryl can further include one or more heteroatoms in the ring wherein one or more of the carbon atoms in the ring are replaced by the one or more heteroatoms, i.e. a heteroaryl.

Another advantage of the presently disclosed ligation reaction is that a wide scope of amino acid substrates are suitable for use. To demonstrate this, salicylaldehyde esters of different Fmoc-amino acids were prepared and their reactivity tested in the ligation reaction. The same was done on the N-terminal residue of the N-hydroxy peptide. As seen from Table 1, the ligation junction sites are not limited to just some specific amino acids. In fact, almost all the tested amino acids are tolerated. In the case of N-termini of N-hydroxy peptides, except for the much hindered Val, both small sized amino acids such as Ala and Gly and larger ones such as Phe and Leu are suitable substrates for the ligation reaction (Table 1, entries 1-5). Regarding the C-terminal residue of the salicylaldehyde ester, the small sized Ala and larger sized Phe, Leu and even Val residues are tolerated (Table 1, entries 6-8). It is noteworthy that large sized amino acids at both sides of the ligation junction also work in the ligation reaction. For example, ligation proceeded smoothly at Leu-Leu and Phe-Leu junctions with good yields (Table 1, entries 10-11).

TABLE 1

Illustrated Scope of N-hydroxyl Assisted Aldehyde Capture Ligation

a

TABLE 1-continued

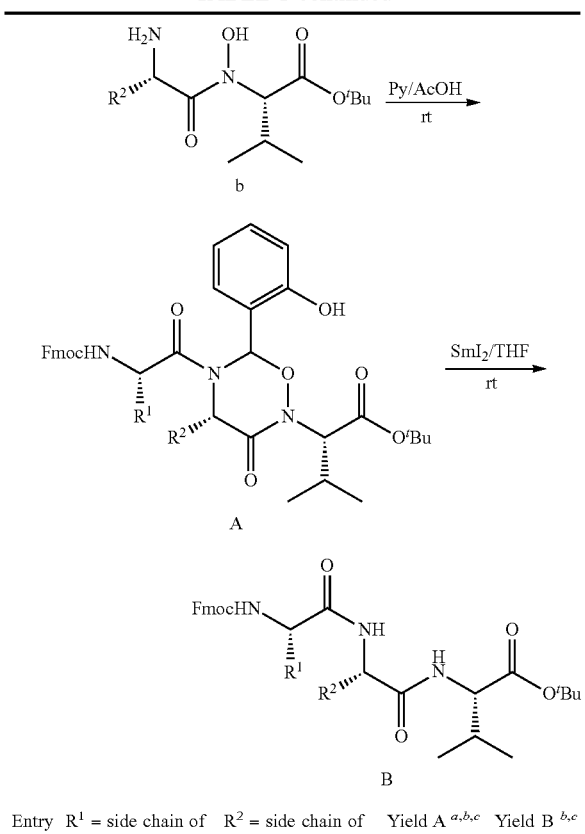

| Entry | $R^1$ = side chain of | $R^2$ = side chain of | Yield A [a,b,c] | Yield B [b,c] |
|---|---|---|---|---|
| 1 | Ala | Ala | 88% | 85% |
| 2 | Ala | Gly | 90% | 80% |
| 3 | Ala | Phe | 92% | 87% |
| 4 | Ala | Leu | 90% | 82% |
| 5 | Ala | Val | — | — |
| 6 | Phe | Ala | 89% | 88% |
| 7 | Leu | Ala | 86% | 84% |
| 8 | Val | Ala | 83% | 80% |
| 9 | Val | Gly | 90% | 87% |
| 10 | Leu | Leu | 73% | 80% |
| 11 | Phe | Leu | 70% | 86% |

[a] Reactions were carried out on a 0.2 mmol scale of both a and b in 1 mL mixture of pyridine/acetic acid (1:1) at rt.
[b] HPLC isolated yield.
[c] Reaction time was 2-5 hours for both steps.

Therefore, in illustrative embodiments, at least one of $R^1$ or $R^3$ is independently a $CH_3$, $CH(CH_3)_2$, $CH_2CH(CH_3)_2$, $CH(CH_3)CH_2CH_3$, $(CH_2)_2$—S—$CH_3$, $CH_2$—SH, $CH_2$—OH, CHOH—$CH_3$, $CH_2$-(3-indolyl), $CH_2$-phenyl, $(CH_2)_4$—$NH_2$, $(CH_2)_3$—NH—C(=NH)$NH_2$, $CH_2$-1H-imidazol-4-yl, $CH_2$-(p-hydroxy-phenyl), $CH_2$—C(O)$NH_2$, $(CH_2)_2$—C(O)$NH_2$, $CH_2$—COOH, and $(CH_2)_2$—COOH, or $R^1$ is $(CH_2)_3$ that forms together with the nitrogen of the adjacent backbone imino group a 5-membered heteroalicyclic ring.

In further various embodiments, $R^2$ is selected from the group consisting of H, $CH_3$, $CH(CH_3)_2$, $CH_2CH(CH_3)_2$, $CH(CH_3)CH_2CH_3$, $(CH_2)_2$—S—$CH_3$, $CH_2$—SH, $CH_2$—OH, CHOH—$CH_3$, $CH_2$-(3-indolyl), $CH_2$-phenyl, $(CH_2)_4$—$NH_2$, $(CH_2)_3$—NH—C(=NH)$NH_2$, $CH_2$-1H-imidazol-4-yl, $CH_2$-(p-hydroxy-phenyl), $CH_2$—C(O)$NH_2$, $(CH_2)_2$—C(O)$NH_2$, $CH_2$—COOH, and $(CH_2)_2$—COOH. In yet further various embodiments, in cases where $R^2$ is $CH_2$—SH, $CH_2$—OH or CHOH—$CH_3$, the thiol or hydroxyl side-chain is protected with a protecting group.

In certain embodiments, at least one of $R^1$, $R^2$ and $R^3$ is independently selected from the group consisting of $CH_3$, $CH_2$-phenyl, $CH_2CH(CH_3)_2$, $CH(CH_3)_2$ and H. For example, $R^1$ is $CH_3$ and $R^2$ is $CH_3$;
$R^1$ is $CH_3$ and $R^2$ is H;
$R^1$ is $CH_3$ and $R^2$ is $CH_2$-phenyl;
$R^1$ is $CH_3$ and $R^2$ is $CH_2CH(CH_3)_2$;
$R^1$ is $CH_2$-phenyl and $R^2$ is $CH_3$;
$R^1$ is $CH_2CH(CH_3)_2$ and $R^2$ is $CH_3$;
$R^1$ is $CH(CH_3)_2$ and $R^2$ is $CH_3$;
$R^1$ is $CH(CH_3)_2$ and $R^2$ is H;
$R^1$ is $CH_2CH(CH_3)_2$ and $R^2$ is $CH_2CH(CH_3)_2$; or
$R^1$ is $CH_2$-phenyl and $R^2$ is $CH_2CH(CH_3)_2$.

The herein described ligation method is extended to the synthesis of peptide segments. Currently salicylaldehyde esters are prepared using solution synthesis, which is laborious and time-consuming and certainly not viable for large peptides. To alleviate this problem, the present inventors have developed a solid phase synthesis method for the preparation of salicylaldehyde ester peptides as shown in Scheme 3. Standard Boc chemistry (where Boc represents di-tert-butyldicarbonate protecting group) is used to assemble the peptide sequence on the 2-hydroxycinnamamide linker and hydrofluoric acid (HF) cleavage then yields the peptidyl 2-hydroxycinnamamide phenolic ester. Ozonolysis of the C=C bond generates the desired aldehyde function in a very short reaction time. This scheme provides a convenient and robust approach to the synthesis of peptide salicylaldehyde esters. As shown in later discussion, this approach is also crucial for the use of the salicylaldehyde ester-mediated ligation in cyclic peptide synthesis.

Scheme 3. Solid Phase Synthesis Approach to Prepare Peptide Salicylaldehyde Esters.

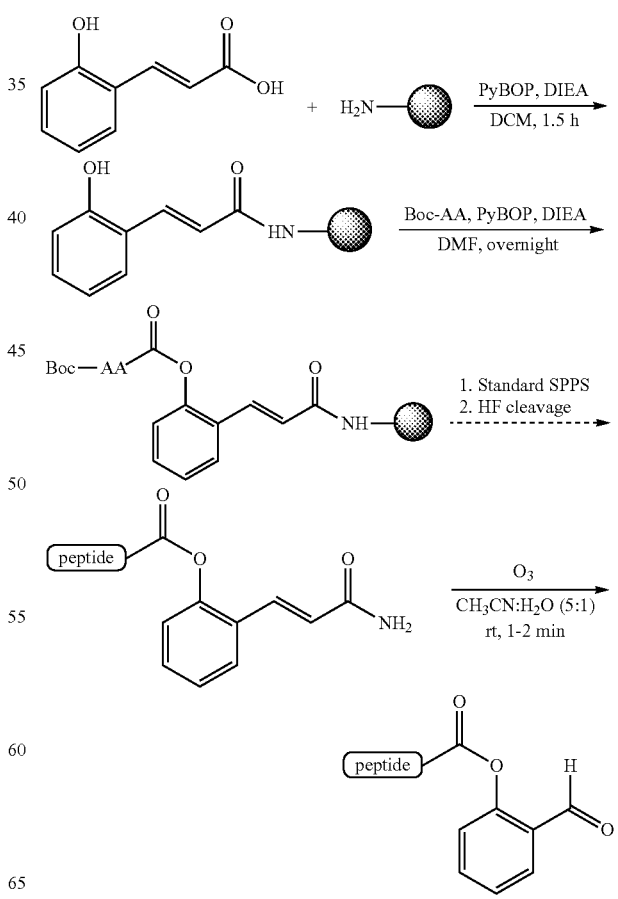

For the other ligation partner, the Fmoc-protected dipeptide, Fmoc-Xaa$_1$-(N$^\alpha$—OH-Xaa$_2$)—OH, was used for the last-step coupling reaction during the solid phase synthesis of peptides containing an N$^\alpha$-hydroxy-aminoacid residue at the second position. As shown in Scheme 4, the Fmoc-dipeptides are prepared by coupling an Fmoc-aminoacyl chloride to an N$^\alpha$-hydroxy-amino acid t-butyl ester in the presence of NaHCO$_3$. Under these conditions, the coupling is specific on the nitrogen of the hydroxylamine derivative. The t-butyl ester is deprotected with trifluoroacetic acid (TFA) to give the free carboxyl. The N$^\alpha$-hydroxy-amino acid t-butyl ester itself is synthesized according to literature procedures, which basically takes three steps starting from the t-butyl ester of an appropriate amino-acid (Scheme 4, top box).

Synthesis of Fmoc—Xaa$_1$—(N$^\alpha$—OH—Xaa$_2$)—OH for Use in Solid Phased Coupling.

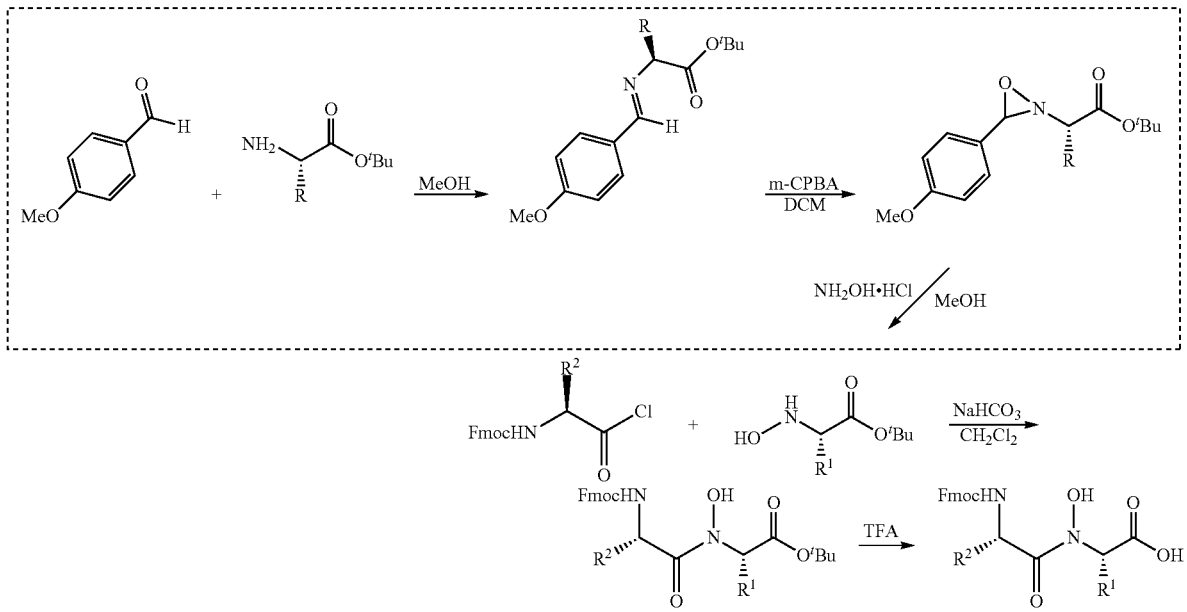

A number of peptide salicylaldehyde esters and aminoacyl-N-hydroxypeptides were prepared and used as substrates in the ligation reactions. The results are summarized in Table 2. It is important to note that the yields are isolated yields from HPLC purification. The actual conversion yields were much higher (>85%) for both the ligation (A) and deprotection (B) steps. The low reaction scales used (about 10-15 μmoles) had a negative effect on the isolated yields due to loss of sample during HPLC purification and perhaps some problems of peptide complexation to SmI$_2$. It should also be noted that the amino acids at the ligation junctions are all non-functionalized at their side chains. These results indeed demonstrate the potential of presently disclosed ligation method as a useful strategy for peptide and protein synthesis.

TABLE 2

Application in Peptide Ligation

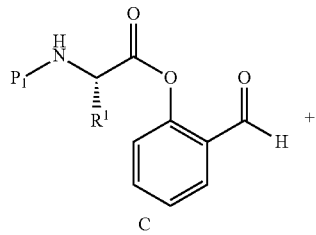

TABLE 2-continued

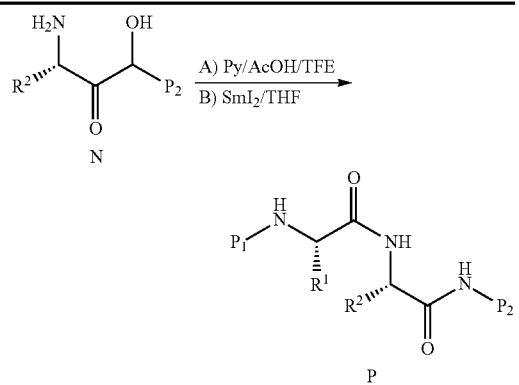

| Entry | Sequence ID | Peptide substrates | Yield A[a] | Yield B[a] |
|---|---|---|---|---|
| 1 | N/A<br>NO: 1<br>NO: 2 | C: Fmoc-Ala-OPhCHO<br>N: H-G(HO-Ala)GVGLFA-NH$_2$<br>P: Fmoc-A-GAGVGLFA-NH$_2$ | 60% | 44% |
| 2 | NO: 3<br>NO: 4<br>NO: 5 | C: Ac-LGFAG-OPhCHO<br>N: H-G(HO-Ala)GVSAG-NH$_2$<br>P: Ac-LGFAG-GAGVSAG-NH$_2$ | 72% | 43% |
| 3 | NO: 3<br>NO: 1<br>NO: 6 | C: Ac-LGFAG-OPhCHO<br>N: H-G(HO-Ala)GVGLFA-NH$_2$<br>P: Ac-LGFAG-GAGVGLFA-NH$_2$ | 66% | 37% |
| 4 | NO: 3<br>NO: 7<br>NO: 8 | C: Ac-LGFAG-OPhCHO<br>N: H-F(HO-Ala)GVGLFA-NH$_2$<br>P: Ac-LGFAG-FAGVGLFA-NH$_2$ | 67% | 38% |
| 5 | NO: 3<br>NO: 9<br>NO: 10 | C: Ac-LGFAG-OPhCHO<br>N: H-L(HO-Ala)GVSAG-NH$_2$<br>P: Ac-LGFAG-LAGVSAG-NH$_2$ | 52% | 38% |

[a] all yields are isolated yields from HPLC purification. For entry 5, ligation was also performed in pyridine/propionic acid or pyridine/isobutyric acid and the isolated yield was 55% and 60%, respectively.

Thus, another aspect of the present disclosure relates to a method of preparing a C-terminal salicylaldehyde ester peptide in solid phase, comprising:
(i) mixing 2-hydroxycinnamic acid and 4-methylbenzhydrylamine hydrochloride salt (MBHA) resin in the presence of benzotriazol-1-yl-oxytripyrrolidinophosphonium hexafluorophosphate (PyBOP) and a tertiary amine to form a 2-hydroxycinnamamide linker on the resin;
(ii) coupling a Boc-amino acid to the 2-hydroxycinnamamide linker-resin, followed by standard BOC solid phase peptide synthesis to form a peptidyl 2-hydroxycinnamamide phenolic ester on the resin, where Boc represents tert-butoxycarbonyl protecting group;
(iii) adding a cleavage agent to release the peptidyl 2-hydroxycinnamamide phenolic ester from the resin; and
(iv) ozonizing the C=C bond of the peptidyl 2-hydroxycinnamamide phenolic ester to obtain the C-terminal salicylaldehyde ester peptide.

In one embodiment, the tertiary amine is diisopropylethylamine (DIEA).

In various embodiments, the cleavage agent comprises an acid or an acid mixture. In one embodiment, the cleavage agent is hydrofluoric acid. In another embodiment, the cleavage agent is trifluoromethanesulfonic acid-trifluoroacetic acid mixture.

The use of presently disclosed salicylaldehyde ester-mediated ligation in cyclic peptide synthesis is next discussed. Specifically, cyclic peptides are synthesized whereby the salicylaldehyde ester and the aminoacyl-N-hydroxyl moiety are placed in the same peptide. Known for their conformational rigidity and resistance to enzymatic degradation, cyclic peptides have much significant therapeutic potential as compared to their linear counterparts. There have been many successful examples in the development of cyclic peptide-based drugs, such as cyclosporine A, vancomycin, Gramicidin S. In particular, cyclic peptides offer a unique opportunity to modulate protein-protein interactions. The large rings of the cyclic peptides provide an excellent scaffold for displaying sufficient numbers of pharmacophoric groups to capture the extensive interactions present at the large interface of two binding proteins. Therapeutic targets involving interactions of this type are difficult to tackle with a small-molecule approach. Therefore cyclic peptides may overtake small molecules as the preferred therapeutic modality for targets of this complexity level. Synthetically, cyclic peptides are notoriously difficult to prepare by traditional methods. Increasingly these molecules are now prepared by chemical ligation approaches. The method described herein has great potential for this application because the ligation sites are not restricted to any particular amino acid as, for instance, in the case of Cys-mediated ligation. With a convenient solid phase synthesis method to prepare peptide salicylaldehyde esters, using the presently disclosed ligation method for cyclic peptide synthesis becomes rather straightforward.

Therefore, in accordance with a further aspect, a method of preparing a serinyl- or threonyl-containing cyclic peptide of formula (6)

(6)

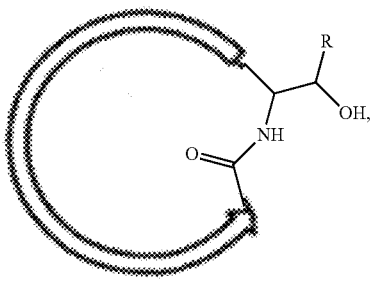

where the peptide contains serine (Ser) or threonine (Thr), comprising:
reacting the C-terminal Ser- or Thr-containing salicylaldehyde ester peptide of formula (1B)

(1B)

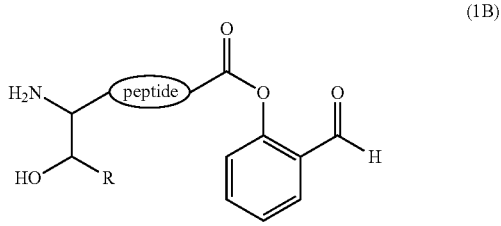

in a pyridine/organic acid mixture; and
adding an acidic deprotecting agent to form the serinyl- or threonyl-containing cyclic peptide of formula (6),
wherein R is a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl, or a side chain of an amino acid.

The acidic deprotecting agent to deprotect the oxazolidine ring may be trifluoroacetic acid (TFA). In this case, no reducing agent is needed to open up the oxazolidine ring obtained from the Ser/Thr cyclization reaction. Advantageously, only TFA is needed to cleave the ring and remove the salicylaldehyde auxiliary moiety to give a natural Ser/Thr residue at the cyclization junction.

The organic acid may be selected as discussed in previous paragraphs. In one embodiment, the organic acid is acetic acid. In another embodiment, the organic acid is propionic acid. In yet another embodiment, the organic acid is isobutyric acid. In a yet further embodiment, the organic acid is butyric acid.

To illustrate the ligation mediation of salicylaldehyde ester at Ser/Thr, cyclization on serinyl- or threonyl-peptide salicylaldehyde esters which were prepared by present solid phase approach was first performed. The overall strategy of this cyclization method is illustrated in the synthesis of Mahafacyclin B, a naturally occurring cyclic heptapeptide from Jatropha mahafalensis (Scheme 5). The salicylaldehyde ester of the peptide Thr-Phe-Phe-Gly-Phe-Phe-Gly (SEQ ID NO:17) was prepared using present solid phase synthesis method. The cyclization reaction was then conducted in a solvent mixture containing 50% pyridine/acidic acid (1/1 molar ratio) and 50% TFE. The use of TFE helped to solubilize the peptide which is rather hydrophobic. The reaction gave a very clean cyclic product with no significant side products detected. The salicylaldehyde acetal moiety was deprotected by TFA to give native Mahafacyclin B with the Thr residue generated at the cyclization junction. Several other cyclic peptides ranging from 4 to 8 amino acid residues were prepared in a similar way (Table 3). The yields were isolated yields from the two reaction steps. For the cyclization of the tetrapeptide (entry 6), a high dilution was employed to prevent intermolecular ligation because the constraints imposed by the small ring size make the intramolecular reaction much more difficult.

Scheme 5. Strategy for the Sythesis of Mahafacyclin B Using Salicylaldehyde-Thr Ligation.

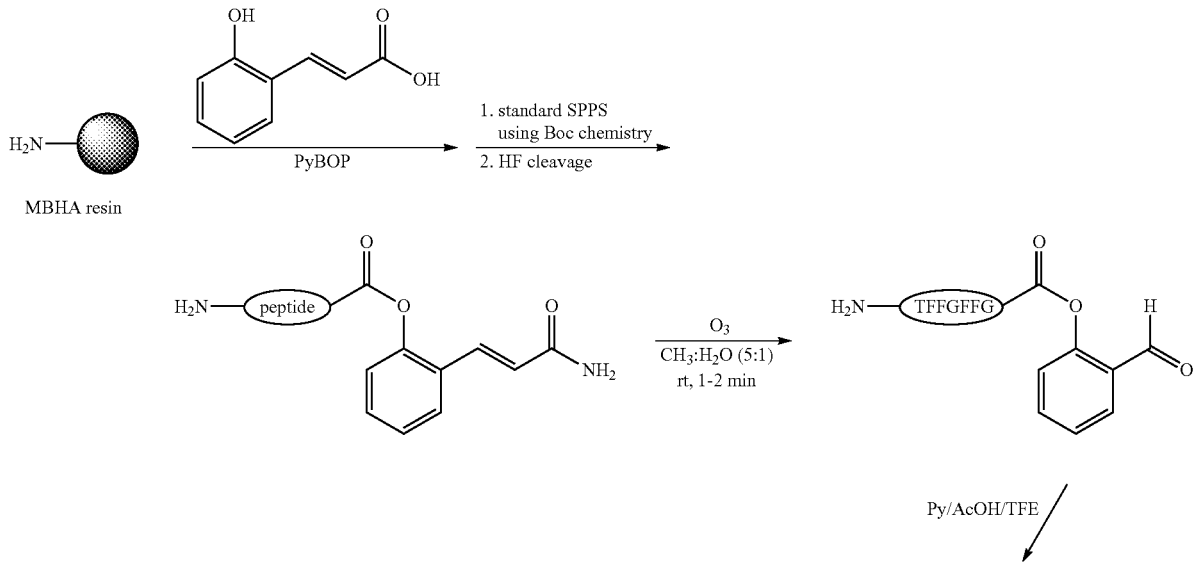

-continued

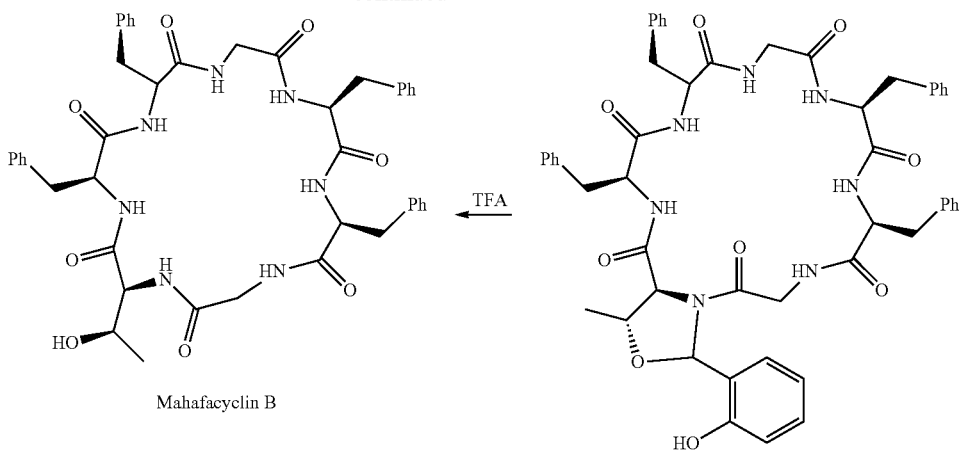

Mahafacyclin B

TABLE 3

Synthesis of Ser- or Thr-Containing Cyclic Peptides

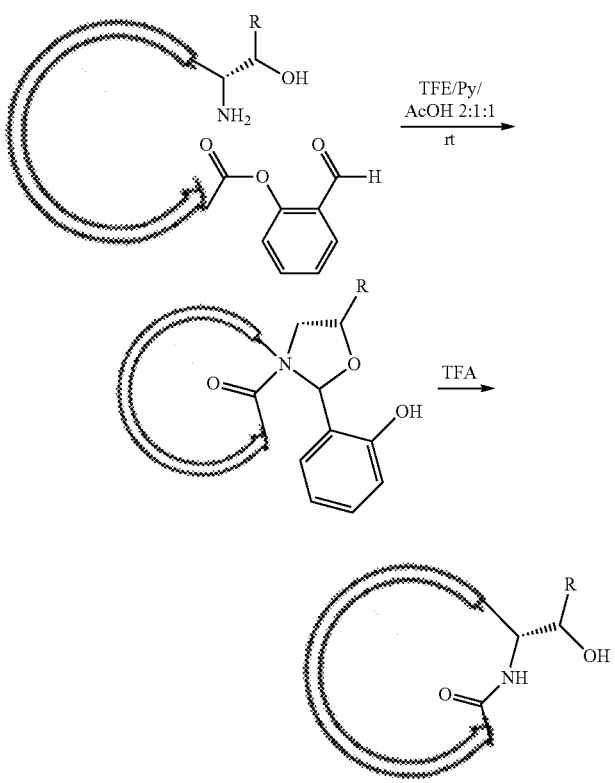

| Entry | Sequence ID | peptide | yield |
|---|---|---|---|
| 1 | SEQ ID NO:11 | SGKAFL | 39% |
| 2 | SEQ ID NO:12 | SFLFA | 35% |
| 3 | SEQ ID NO:13 | TGLFGFAG | 63% |
| 4 | SEQ ID NO:14 | SGLFGFAG | 65% |
| 5 | SEQ ID NO:15 | SGLYGFAG | 52% |
| 6 | SEQ ID NO:16 | SLSL | 20% |
| 7 | SEQ ID NO:17 | TFFGFFG | 56% | b. Present N-hydroxyl mediated salicylaldehyde ligation method for cyclic peptide synthesis was used (Scheme 6). In order to do this, the salicylaldehyde ester must have an N-hydroxylaminoacid at the second position from the N-terminus. This N-hydroxyamino acid should be coupled in the Boc protected form. The N-Boc-N- benzyl oxy-amino acids (Scheme 6) was prepared for this purpose.

Scheme 6. Strategy for Peptide Cyclization Using N-hydroxyl Medicated Salicylaldehyde Ligation

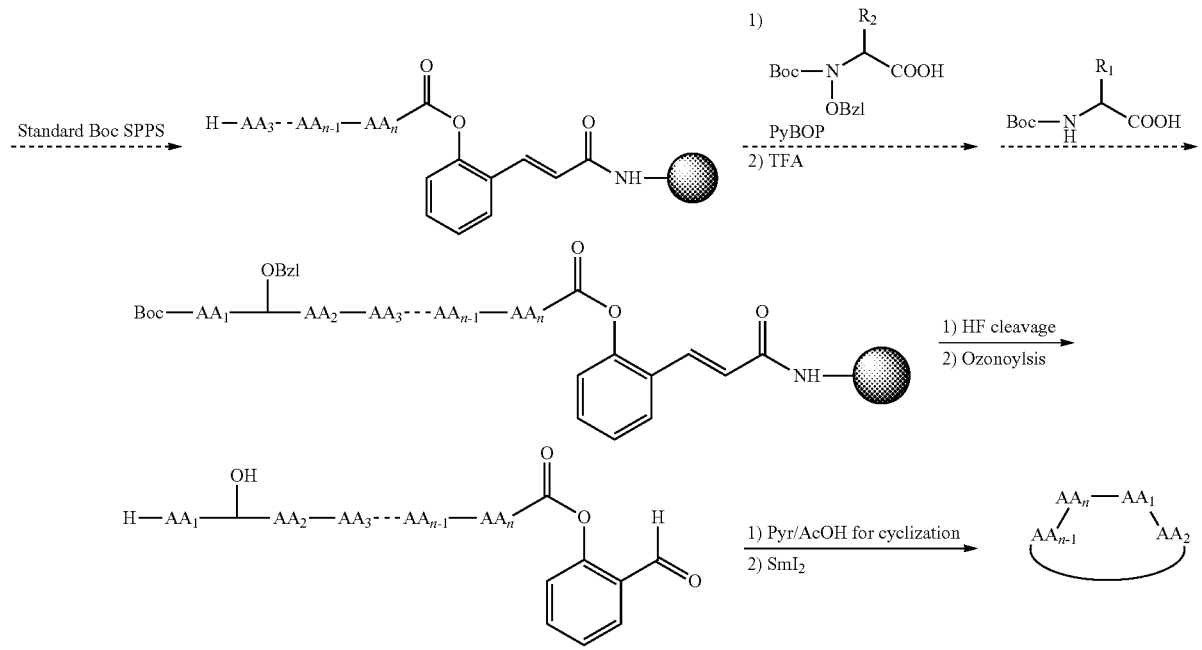

Thus, in yet another aspect, there is disclosed a method of preparing a cyclic peptide of formula (5)

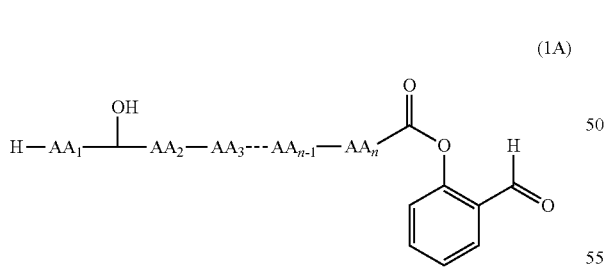

(5)

where $AA_n$ represents an amino acid at a $n^{th}$ position of the peptide,
comprising:
reacting the C-terminal salicylaldehyde ester peptide of formula (1A)

(1A)

in a pyridine/organic acid mixture, where " - - - " represents additional amino acids in the chain of the peptide; and
adding a reducing agent to form the cyclic peptide of formula (5).

The reducing agent may be selected as discussed in previous paragraphs. In one embodiment, the reducing agent is $SmI_2$ solution, such as $SmI_2$ solution in THF or $SmI_2$ solution in TFE.

The organic acid may be selected as discussed in previous paragraphs. In one embodiment, the organic acid is acetic acid.

In a further aspect, there is provided a method of preparing a polypeptide or protein of formula (7)

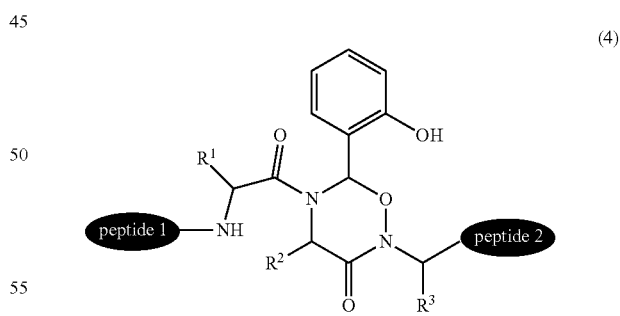

(7)

comprising reacting a compound of formula (4)

(4)

with trifluoroacetic acid (TFA),
wherein each of $R^1$, $R^2$ and $R^3$ is independently selected from the group consisting of H, a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl, and a side chain of an amino acid.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numberical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

In order that the invention may be readily understood and put into practical effect, particular embodiments will now be described by way of the following non-limiting examples.

EXAMPLES

Methodology and Experimental Procedures

General Methods.

Unless otherwise noted, all reactions were carried out in oven dried glassware under an atmosphere of nitrogen and distilled solvents were transferred by syringe. Solvents and reagents were purified according to the standard procedure prior to use. Evaporation of organic solutions was achieved by rotary evaporation with a water bath temperature below 40° C. Product purification by flash column chromatography was accomplished using silica gel 60 (0.010-0.063 nm). Technical grade solvents were used for chromatography and distilled prior to use. NMR spectra were recorded at room temperature on a 400 MHz Bruker DPX 400 spectrometers, respectively. The residual solvent signals were taken as the reference (7.26 ppm for $^1$H NMR spectroscopy and 77.0 ppm for $^{13}$C NMR spectroscopy). Chemical shift ($\delta$) is referred in terms of ppm, coupling constants (J) are given in Hz. Following abbreviations classify the multiplicity: s=singlet, d=doublet, t=triplet, q=quartet, m=multiplet or unresolved, br=broad signal. Infrared spectra were recorded on a Bio-RAD FTS 165 FT-IR Spectrometer and reported in $cm^{-1}$. Samples were prepared in thin film technique. HRMS (ESI) spectra were recorded on a Finnigan/MAT LCQ quadrupole ion trap mass spectrometer, coupled with the TSP4000 HPLC system and the Crystal 310 CE system.

Amino acid derivatives, coupling reagents and resins were purchased from GL Biochem (Shanghai, China) or Novabiochem. All the other chemical reagents were purchased from Alfa Aesar, Sigma-Aldrich Chemical Company, Fisher Scientific, Acros Organics. All the analytic HPLC analyses were performed by using an Agilent 1100 series instrument equipped with a Jupiter C18 (5 um, 4.6×250 mm) reverse-phase column. Detection was achieved with a UV-VIS-detector at wavelength $\lambda$=220 nm. A typical gradient used for analysis was buffer B rising 2% every minute starting from 0%. The purification was performed using a semi-preparative HPLC column on a Shimadzu system equipped with a vydac C18 column (5 um, 10×250 mm) with a flow rate of 2.5 ml/min. The buffer system for all the analysis was buffer A-$H_2O$ (containing 0.045% TFA) and buffer B-90% acetonitrile in $H_2O$ (containing 0.04% TFA). Peptide masses were measured using a Thermo FINNIGAN LCQ Deca XP MAX equipped with ESI ion source.

Example 1

Procedure for the Preparation of N-Hydroxy-α-L-Amino Acid t-Butyl Esters

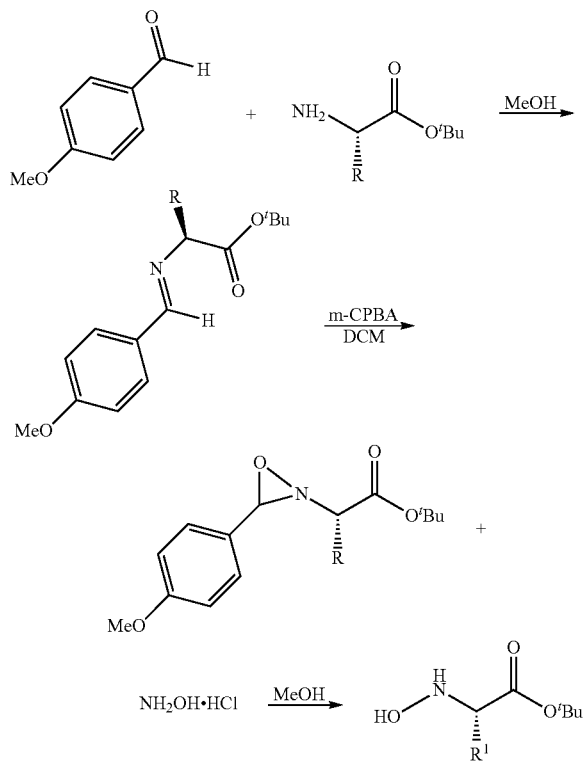

To a solution of the α-L-amino acid t-Butyl ester hydrochloride in methanol is added 4-methoxybenzaldehyde and dry Na$_2$CO$_3$. The mixture is stirred for 12 h at room temperature, filtered, and evaporated. The residue is dissolved in Et$_2$O and this solution is filtered and evaporated to give the Schiff base; yield: ~100%.

The Schiff base is dissolved in dry CH$_2$Cl$_2$, this solution is cooled to −15° C., and a solution of 3-chloroperoxybenzoic acid (MCPBA, 77%) in dry CH$_2$Cl$_2$ is added dropwise. Stirring is continued for 14 h at room temperature. The precipitated 3-chlorobenzoic acid is filtered off and the filtrate is washed with saturated NaHCO$_3$ solution and with water, dried (MgSO$_4$), and evaporated to give the crude oxaziridine; yield: ~100%.

The oxaziridine is dissolved in MeOH, hydroxylamine hydrochloride is added, and the mixture is stirred for 12 h at room temperature. The solvent is then evaporated and water is added. The solution is extracted with Et$_2$O twice, this Et$_2$O extract being discarded. The aqueous phase is saturated with NaHCO$_3$ (Caution: vigorous foam evolution) and the free N-hydroxy-α-L-amino acid t-Butyl ester is extracted with Et$_2$O. The organic layer is dried (MgSO$_4$) and the product is isolated by evaporation.

Analytical Data of the Compounds Prepared by the Procedure of Example 1

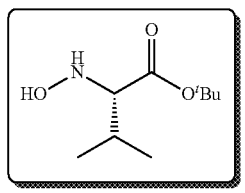

(9-tert-butyl 2-(hydroxyamino)-3-methylbutanoate

Yield for three steps: 45%, pale yellow solid. $^1$H NMR (400 MHz, CDCl$_3$): δ 3.30 (d, J=6.8 Hz, 1H), 1.87 (m, 1H), 1.49 (s, 9H), 0.95 (d, J=6.8 Hz, 6H) ppm; $^{13}$C NMR (100 MHz, CDCl$_3$): δ 172.8, 81.5, 71.7, 29.0, 28.1, 19.3, 19.2 ppm; FTIR (KBr, neat): v 3263, 3194, 2978, 1736, 1465, 1367, 1219, 1149, 1026 cm$^{-1}$; HRMS (ESI, m/z) calcd for C$_9$H$_{19}$NO$_3$H$^+$: 190.1443. found: 190.1450.

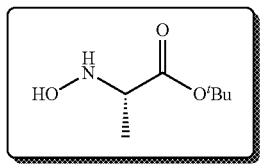

(S)-tert-butyl 2-(hydroxyamino)propanoate

Yield for three steps: 76%, pale yellow solid. NMR (400 MHz, CDCl$_3$): δ 3.58 (q, J=7.2 Hz, 1H), 1.46 (s, 9H), 1.21 (d, J=6.8 Hz, 3H) ppm; $^{13}$C NMR (100 MHz, CDCl$_3$): δ 173.3, 81.6, 60.9, 28.0, 14.6 ppm; FTIR (KBr, neat): v 3257, 3194, 2978, 1743, 1458, 1365, 1219, 1157, 1103 cm$^{-1}$; HRMS (ESI, m/z) calcd for C$_7$H$_{15}$NO$_3$H$^+$: 162.1130. found: 162.1129.

Example 2

Procedure for the Preparation of Unprotected N—OH Dipeptide t-Butyl Esters

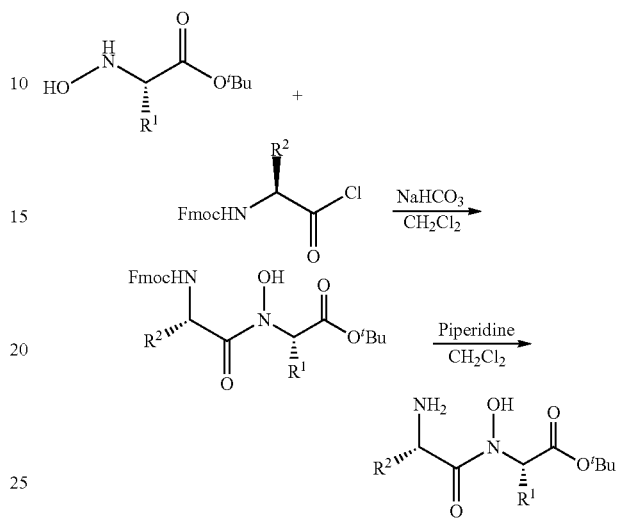

To the mixture of N-hydroxy-α-L-amino acid t-Butyl esters (1 equiv.) and Fmoc amino acid chloride (1 equiv.) in dichloromethane was added 3 equiv. of NaHCO$_3$ slowly at room temperature. The mixture was stirred at room temperature for 1-2 hours monitored by TLC. Water was added to the reaction mixture and the aqueous layer was extracted with CH$_2$Cl$_2$ for twice. The organic layer was collected and washed with brine, dried over Na$_2$SO$_4$ and solvent was removed in vacuo. The residue was purified by column chromatography (silica gel, hexanes/EtOAc/DCM) to give the Fmoc protected N—OH dipeptide t-Butyl ester as white solid. Fmoc protected N—OH dipeptide t-Butyl ester was de-protected by treatment of piperidine in dichloromethane. The reaction mixture was poured into a mixture of MeCN/H$_2$O. With the evaporation of CH$_2$Cl$_2$ under the help of a stream of nitrogen, the side product was precipitated as white solid. The precipitate was removed by filtration and the filtrate was injected to preparative reverse phase HPLC to afford the pure unprotected N—OH dipeptide t-Butyl esters.

Analytical Data of the Compounds Prepared by the Procedure of Example 2

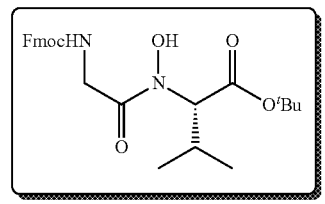

(S)-tert-butyl-2-(2-(((9H-fluoren-9-yl)methoxy)carbonylamino)-N-hydroxyacetamido)-3-methylbutanoate Yield: 95%, white solid. $^1$H NMR (400 MHz, CDCl$_3$): δ 7.78-7.74 (m, 2H), 7.63-7.59 (m, 2H), 7.43-7.36 (m, 2H), 7.34-7.28 (m, 2H), 5.66-5.58 (m, 1H), 4.90 (d, J=7.6 Hz, 1H), 4.38 (d, J=7.1 Hz, 2H), 4.30-4.20 (m, 3H), 2.44-2.34 (m, 1H), 1.49 (s, 9H), 1.06 (d, J=6.8 Hz, 3H), 1.03 (d, J=6.8 Hz, 3H) ppm; $^{13}$C NMR (100 MHz, CDCl$_3$): δ 171.8, 169.4, 156.4, 143.9, 141.3, 127.7, 127.1, 125.2, 119.9, 83.9, 67.2, 63.2, 47.1, 42.2, 29.4, 28.0, 19.6, 19.4 ppm; FTIR (KBr, neat): v 3449, 3287, 2978, 1728, 1659, 1450, 1373, 1273, 1150 cm$^{-1}$; HRMS (ESI, m/z) calcd for C$_{26}$H$_{32}$N$_2$O$_6$H$^+$: 469.2339. found: 469.2334.

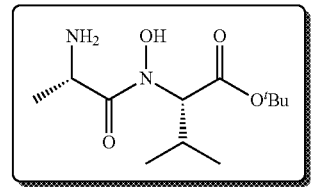

(S)-tert-butyl 2-((S)-2-amino-N-hydroxypropanamido)-3-methylbutanoate

Yield: 52%, white solid. NMR (400 MHz, CDCl$_3$): δ 8.11 (bs, 1H), 4.73-4.67 (m, 1H), 4.64 (d, J=7.5 Hz, 1H), 2.41-2.28 (m, 1H), 1.54 (d, J=6.8 Hz, 3H), 1.46 (s, 9H), 1.01 (d, J=6.2 Hz, 3H), 0.96 (d, J=6.2 Hz, 3H) ppm; $^{13}$C NMR (100 MHz, CDCl$_3$): δ 170.2, 169.9, 83.5, 64.8, 44.7, 28.1, 27.9, 19.2, 15.5 ppm; FTIR (KBr, neat): v 3503, 3132, 2985, 1751, 1667, 1474, 1373, 1196, 1150 cm$^{-1}$; HRMS (ESI, m/z) calcd for C$_{12}$H$_{24}$N$_2$O$_4$H$^+$: 261.1814. found: 261.1835.

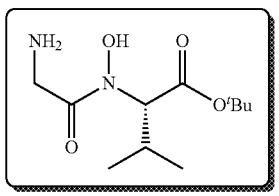

(S)-tert-butyl 2-(2-amino-N-hydroxyacetamido)-3-methylbutanoate

Yield: 47%, white solid. $^1$H NMR (400 MHz, CDCl$_3$): δ 8.18 (bs, 1H), 4.67 (d, J=8.3 Hz, 1H), 4.19-4.08 (m, 2H), 3.10 (bs, 1H), 2.42-2.30 (m, 1H), 1.84-1.76 (m, 1H), 1.45 (s, 9H), 0.99 (d, J=6.8 Hz, 3H), 0.96 (d, J=6.8 Hz, 3H) ppm; $^{13}$C NMR (100 MHz, CDCl$_3$): 170.0, 167.7, 83.4, 64.9, 44.7, 40.1, 28.5, 27.8, 22.5, 19.2 ppm; FTIR (KBr, neat): v 3101, 2978, 1682, 1474, 1203, 1142 cm$^{-1}$; HRMS (ESI, m/z) calcd for C$_{11}$H$_{22}$N$_2$O$_4$H$^+$: 247.1658. found: 247.1667.

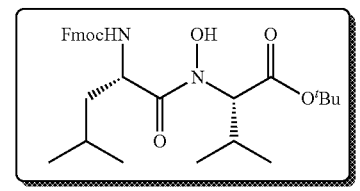

(S)-tert-butyl-2-((S)-2-(((9H-fluoren-9-yl)methoxy)carbonylamino)-N-hydroxy-4-methylpentanamido)-3-methylbutanoate Yield: 92%, white solid. NMR (400 MHz, CDCl$_3$): δ 7.80-7.72 (m, 2H), 7.63-7.55 (m, 2H), 7.42-7.36 (m, 2H), 7.33-7.27 (m, 2H), 5.49 (d, J=8.9 Hz, 1H), 5.09-5.01 (m, 1H), 4.88-4.84 (m, 1H), 4.35 (d, J=6.0 Hz, 2H), 4.24-4.17 (m, 1H), 2.44-2.31 (m, 1H), 2.06-1.82 (m, 1H), 1.79-1.69 (m, 1H), 1.55-1.44 (m, 11H), 1.06-0.93 (m, 12H) ppm; $^{13}$C NMR (100 MHz, CDCl$_3$): δ 172.7, 171.4, 156.4, 144.0, 143.8, 141.3, 127.7, 127.1, 125.2, 119.9, 83.3, 67.1, 63.2, 49.2, 47.2, 41.6, 29.0, 28.0, 24.8, 23.3, 21.9, 19.5 ppm; FTIR (KBr, neat): v 3302, 2932, 1744, 1697, 1450, 1257, 1157 cm$^{-1}$; HRMS (ESI, m/z) calcd for C$_{30}$H$_{40}$N$_2$O$_6$H$^+$: 525.2965. found: 525.2969.

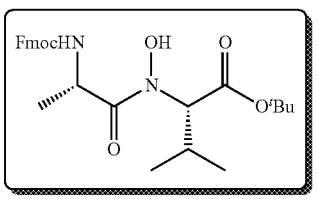

(S)-tert-butyl-2-((S)-2-(((9H-fluoren-9-yl)methoxy)carbonylamino)-N-hydroxypropanamido)-3-methylbutanoate Yield: 92%, white solid. $^1$H NMR (400 MHz, CDCl$_3$): δ 7.81-7.76 (m, 2H), 7.65-7.59 (m, 2H), 7.45-7.38 (m, 2H), 7.36-7.29 (m, 2H), 5.74 (d, J=8.0 Hz, 1H), 5.08-4.98 (m, 1H), 4.90-4.88 (m, 1H), 4.38 (d, J=8.4 Hz, 2H), 4.27-4.20 (m, 1H), 2.44-2.34 (m, 1H), 1.52 (s, 9H), 1.44 (d, J=6.8 Hz, 3H), 1.08 (d, J=6.8 Hz, 3H), 1.05 (d, J=6.8 Hz, 3H) ppm; $^{13}$C NMR (100 MHz, CDCl$_3$): δ 173.1, 171.7, 156.0, 144.1, 141.3, 127.7, 127.1, 125.2, 119.9, 83.5, 67.0, 63.2, 47.1, 46.9, 29.1, 28.0, 19.6, 19.4, 18.4 ppm; FTIR (KBr, neat): v 3302, 2978, 1736, 1690, 1543, 1450, 1373, 1256, 1157 cm$^{-1}$; HRMS (ESI, m/z) calcd for C$_{27}$H$_{34}$N$_2$O$_6$H$^+$: 483.2495. found: 483.2519.

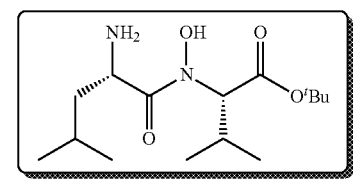

(S)-tert-butyl 2-((S)-2-amino-N-hydroxy-4-methylpentanamido)-3-methylbutanoate

Yield: 62%, white solid. $^1$H NMR (400 MHz, CDCl$_3$): δ 4.73-4.65 (m, 1H), 4.61 (d, J=8.1 Hz, 1H), 3.16-3.08 (m, 1H), 2.42-2.29 (m, 1H), 1.85-1.74 (m, 3H), 1.71-1.61 (m, 1H), 1.46 (s, 9H), 1.03-0.93 (m, 12H), ppm; $^{13}$C NMR (100

MHz, CDCl$_3$): δ 169.9, 169.5, 83.1, 64.8, 49.6, 44.7, 39.3, 27.9, 24.4, 22.8, 22.5, 21.4, 19.3, 19.1 ppm; FTIR (KBr, neat): v 2970, 1682, 1474, 1373, 1204, 1142 cm$^{-1}$; HRMS (ESI, m/z) calcd for C$_{15}$H$_{30}$N$_2$O$_4$H$^+$: 303.2284. found: 303.2310.

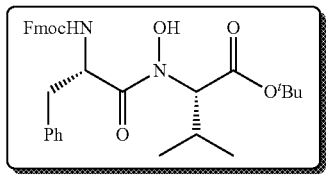

(S)-tert-butyl-2-((S)-2-(((9H-fluoren-9-yl)methoxy) carbonylamino)-N-hydroxy-3-phenylpropanamido)-3-methylbutanoate Yield: 90%, white solid. $^1$H NMR (400 MHz, CDCl$_3$): δ 7.80-7.72 (m, 2H), 7.60-7.55 (m, 2H), 7.43-7.36 (m, 2H), 7.34-7.15 (m, 8H), 5.60 (d, J=8.2 Hz, 1H), 5.32-5.25 (m, 1H), 4.85 (d, J=7.6 Hz, 1H), 4.39 (dd, J=10.3 Hz, J=7.3 Hz, 1H), 4.29 (dd, J=10.3 Hz, J=7.3 Hz, 1H), 4.19 (t, J=7.3 Hz, 1H), 3.12 (dd, J=13.7 Hz, J=6.3 Hz, 1H), 3.01 (dd, J=13.7 Hz, J=6.3 Hz, 1H), 1.03 (d, J=6.8 Hz, 1H), 0.99 (d, J=6.8 Hz, 1H) ppm; $^{13}$C NMR (100 MHz, CDCl$_3$): δ 171.8, 170.9, 155.8, 143.8, 141.3, 136.1, 129.5, 128.5, 127.7, 127.1, 126.9, 125.2, 125.1, 119.9, 83.6, 67.0, 63.0, 51.8, 47.1, 38.4, 29.3, 28.0, 19.6, 19.3 ppm; FTIR (KBr, neat): v 3310, 2970, 1736, 1697, 1628, 1450, 1258, 1157 cm$^{-1}$; HRMS (ESI, m/z) calcd for C$_{33}$H$_{38}$N$_2$O$_6$H$^+$: 559.2808. found: 559.2808.

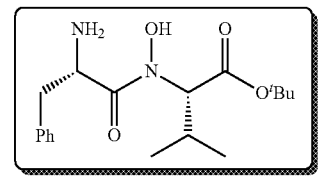

(S)-tert-butyl 2-((S)-2-amino-N-hydroxy-3-phenyl-propanamido)-3-methylbutanoate

Yield: 43%, white solid. $^1$H NMR (400 MHz, CDCl$_3$): δ 7.32-7.22 (m, 5H), 4.91-4.84 (m, 1H), 4.61-4.63 (m, 1H), 3.38-3.29 (m, 1H), 3.09-3.00 (m, 2H), 2.38-2.27 (m, 1H), 1.82-1.73 (m, 1H), 1.48 (s, 9H), 1.00-0.93 (m, 6H), ppm; $^{13}$C NMR (100 MHz, CDCl$_3$): δ 169.5, 168.6, 134.0, 129.6, 129.0, 127.8, 83.1, 64.5, 52.4, 44.6, 35.7, 28.2, 28.0, 19.2 ppm; FTIR (KBr, neat): v 3464, 2988, 1720, 1667, 1458, 1288, 1203, 1134 cm$^{-1}$; HRMS (ESI, m/z) calcd for C$_{18}$H$_{28}$N$_2$O$_4$H$^+$: 337.2127. found: 337.2130.

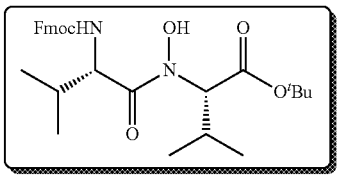

(S)-tert-butyl-2-((S)-2-(((9H-fluoren-9-yl)methoxy) carbonylamino)-N-hydroxy-3-methylbutanamido)-3-methylbutanoate Yield: 94%, white solid. $^1$H NMR (400 MHz, CDCl$_3$): δ 7.78-7.72 (m, 2H), 7.63-7.55 (m, 2H), 7.42-7.36 (m, 2H), 7.33-7.27 (m, 2H), 5.55 (d, J=9.2 Hz, 1H), 4.93-4.86 (m, 1H), 4.42-4.33 (m, 2H), 4.26-4.20 (m, 1H), 2.42-2.32 (m, 1H), 2.17-2.07 (m, 1H), 1.49 (s, 9H), 1.07-0.91 (m, 12H) ppm; $^{13}$C NMR (100 MHz, CDCl$_3$): δ 171.8, 171.4, 156.6, 143.9, 141.3, 127.7, 127.1, 125.2, 119.9, 83.3, 67.1, 63.2, 55.4, 47.2, 30.8, 28.9, 28.1, 28.0, 19.5, 19.4, 17.4 ppm; FTIR (KBr, neat): v 3302, 2970, 1744, 1690, 1543, 1258, 1165, 1034 cm$^{-1}$; HRMS (ESI, m/z) calcd for C$_{29}$H$_{38}$N$_2$O$_6$H$^+$: 511.2808. found: 511.2819.

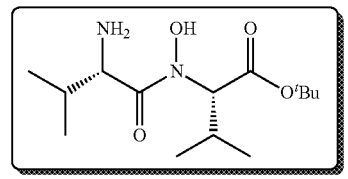

(S)-tert-butyl 2-((S)-2-amino-N-hydroxy-3-methylbutanamido)-3-methylbutanoate

Yield: 40%, white solid. $^1$H NMR (400 MHz, CDCl$_3$): δ 4.65 (d, J=8.2 Hz, 1H), 4.59 (d, J=3.8 Hz, 1H), 2.46-2.28 (m, 2H), 1.46 (s, 9H), 1.09 (d, J=6.8 Hz, 3H), 1.04-0.98 (m, 6H), 0.95 (d, J=6.8 Hz, 3H) ppm; $^{13}$C NMR (100 MHz, CDCl$_3$): δ 169.4, 168.8, 83.1, 64.8, 55.7, 29.0, 27.9, 19.2, 19.1, 18.6, 16.7 ppm; FTIR (KBr, neat): v 3464, 3101, 2970, 1744, 1667, 1473, 1180, 1150 cm$^{-1}$; HRMS (ESI, m/z) calcd for C$_{14}$H$_{28}$N$_2$O$_4$H$^+$: 289.2127. found: 289.2119.

Example 3

Procedure for the Synthesis of N—OH Peptide

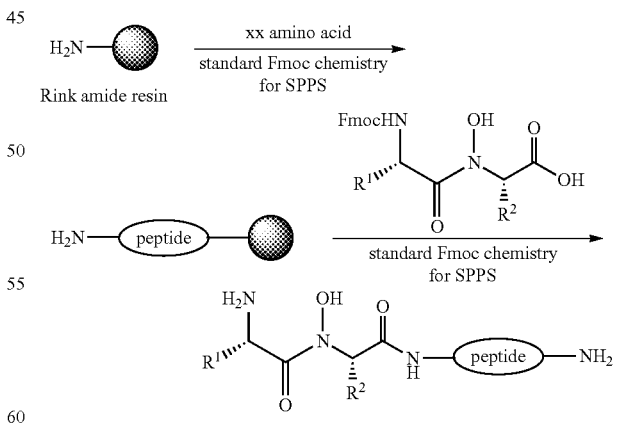

All of the N—OH peptides were manually synthesized employing standard Fmoc solid phase peptide synthesis (SPPS). For the coupling of amino acids, Fmoc-amino acid (4 eq.) and benzotriazol-1-yl-oxytripyrrolidinophosphonium hexafluorophosphate (PyBOP) (4 eq.) were dissolved in DMF. DIEA (8 eq.) was added in the solution. After 2 min of activation, the mixture was mixed with Rink amide MBHA resin (substitution: 0.65 mmol/g). The reaction was undertaken for 1.5 h. The coupling efficiency was checked with ninhydrin test. The Fmoc group was removed by treatment with 20% piperidine in DMF for 10 min, followed by 15 min. The side chain protected amino acid derivatives used were Fmoc-Ser(Bzl)-OH and Fmoc-Thr(Bzl)-OH. For the coupling of the last two amino acid units, N—OH dipeptide acid prepared above was used while not amino acids. After sequence assembly, N—OH peptides were cleaved from the resin with a cocktail solution of TFA/H$_2$O/i-Pr$_3$SiH (95:2.5:2.5). The crude peptides were purified with C18 preparative HPLC.

Example 4

Procedure for Solid Phase Synthesis of C-Terminal Salicylaldehyde Ester Peptides

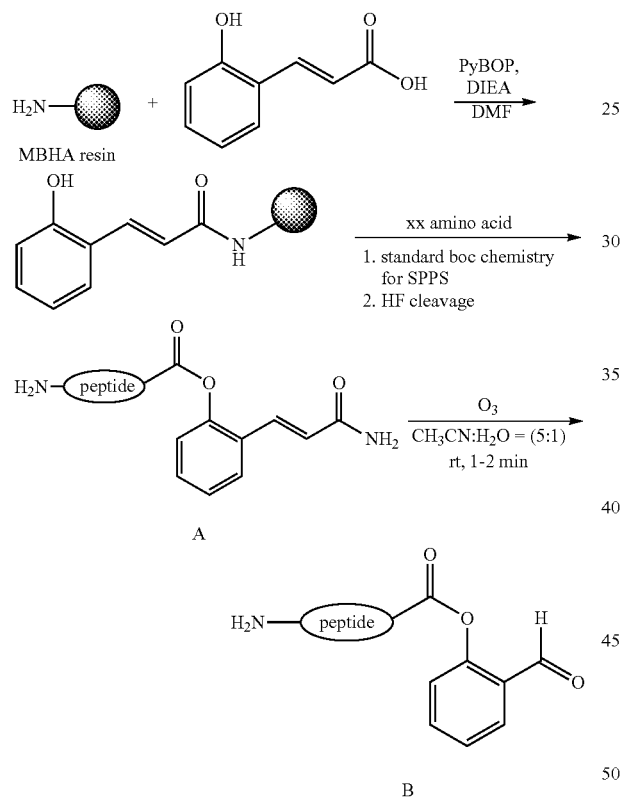

C-terminal salicylaldehyde ester peptides were synthesized manually on solid phase employing standard Boc chemistry. For the coupling of 2-OH-PhCH=CHCOOH, the carboxylic acid (2 eq.) and benzotriazol-1-yl-oxytripyrrolidinophosphonium hexafluorophosphate (PyBOP) (2 eq.) were dissolved in DCM. DIEA (6 eq.) was added in the solution. After 2 min of activation, the mixture was mixed with MBHA resin. The reaction was undertaken for 1.5 h. The coupling efficiency was checked with Ninhydrin test. For the coupling of amino acids, Boc-amino acid (4 eq.) and benzotriazol-1-yl-oxytripyrrolidinophosphonium hexafluoro-phosphate (PyBOP) (4 eq.) were dissolved in DMF. DIEA (8 eq.) was added to the solution. After 2 min of activation, the mixture was mixed with resin. The coupling efficiency was checked with nihydrin test except for the first amino acids. Considering the relative lower coupling efficiency of phenolic hydroxyl group, the mixture was stirred overnight at room temperature for the coupling of the first amino acid. The Boc group was removed by treatment with 30% TFA in DCM for 10 min, followed by 15 min. The side chain protected amino acid derivatives used were Boc-Ser(Bzl)-OH, Boc-Thr(Bzl)-OH. After sequence assembly, the massive resin was cleaved under the standard condition employed by using HF as the reagent. The crude peptides were purified with C18 preparative reverse phase HPLC. The peptide with an α,β-unsaturated penolic ester at the C-terminus was further treated with O$_3$ in a mixture of acetonitrile/water (5:1) for 2 min at room temperature to give C-terminal salicylaldehyde ester peptide. Dimethylsulfide was added to the ozonolysis mixture although it is not necessary. The pure C-terminal salicylaldehyde ester peptide was obtained by purification with C18 preparative reverse phase HPLC. The C-terminal salicylaldehyde ester peptide could also be obtained from direct ozonolysis of the peptide with an α,β-unsaturated penolic ester at the C-terminus on the resin.

Example 5

Procedure for the Ligation

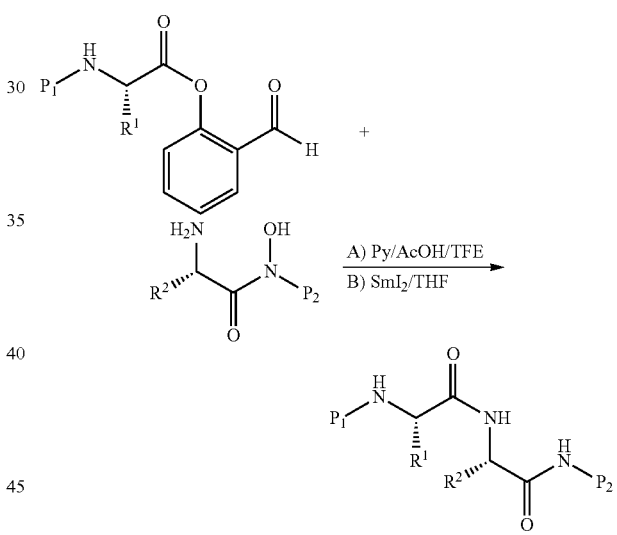

0.01 mmol N—OH peptide (1.0 equiv.) and 0.015 mmol C-terminal salicylaldehyde ester peptide (1.5 equiv.) were dissolved in 0.1 mL of trifluoroethanol (TFE). To the solution was added 0.1 mL of pyridine/acetic acid (1:1 mole/mole). The mixture was stirred at room temperature for 2-5 hours. The reaction was monitored by HPLC and MS. The mixture was injected to C18 semi-preparative HPLC for purification. The ligated intermediate containing a cyclic motif was isolated as a mixture of four isomers by HPLC. After lyophilisation, the ligated intermediate was put into a dry 10 mL round bottomed flask which was blanketed with argon. 0.1 mL of trifluoroethanol was added. Freshly prepared 0.1 M SmI$_2$ in THF was added dropwise until a blue color just persisted (3-5 mL). The reaction was stirred vigorously at room temperature for 2-5 hours and monitored by HPLC and MS. After the completion of the reaction, the mixture was poured into cold water and stirred vigorously for 5 minutes. The precipitate was filtered off and the clear filtrate was injected to C18 semi-preparative HPLC for purification.

Example 6

Procedure for the Synthesis of Cyclic Peptides Using Salicylaldehyde Ester Mediated Ligation at Ser or Thr

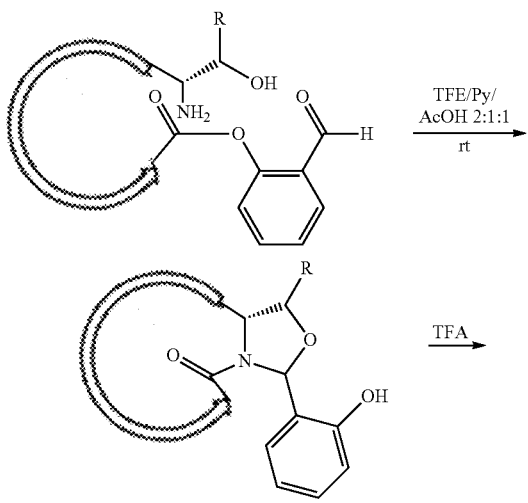

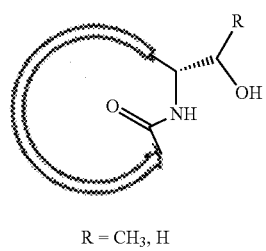

R = CH₃, H

The C-terminal salicylaldehyde ester peptides with a Ser or Thr at the N-terminus were prepared by SPPS using Boc chemistry. For cyclization, typically 0.005 mmol of a peptide was firstly dissolved in 2,2,2-trifluoro ethanol (TFE) (0.25 mL) followed by addition of pyridine/acetic acid (1:1) mixture (0.25 mL). The reaction mixture was stirred at room temperature for 1 to 5 hours and the ligation was monitored by reverse phase HPLC. After removal of the solvent, the residue was treated with a cocktail solution of TFA/H₂O/i-Pr₃SiH (95:2.5:2.5) to generate the final cyclic peptide with a natural peptide bond at the junction site. The crude product was purified by C18 semi-preparative reverse phase HPLC.

---

The invention claimed is:

1. A method of preparing a polypeptide or protein of formula (3)

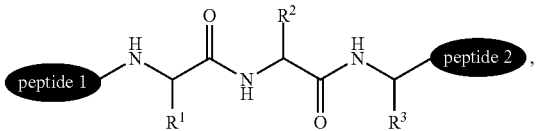

(3)

comprising:

reacting a C-terminal salicylaldehyde ester peptide of formula (1)

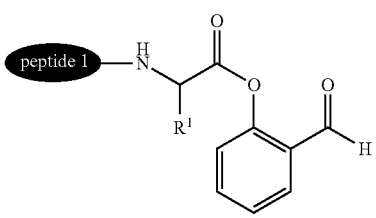

(1)

with an aminoacyl-N-hydroxyl peptide of formula (2)

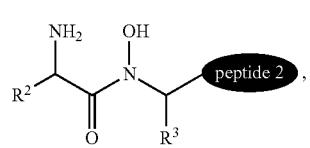

(2)

wherein the reaction is carried out in a pyridine/organic acid mixture to form an intermediate compound having a 1,2,5-oxadiazinane ring structure; and adding a reducing agent to cleave the 1,2,5-oxadiazinane ring structure of the intermediate compound to form the polypeptide or protein of formula (3), wherein each of $R^1$, $R^2$ and $R^3$ is independently selected from the group consisting of H, a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl, and a side chain of an amino acid; or $R^1$ is $C_1$-$C_{10}$ alkylyl that forms together with the nitrogen of the adjacent backbone imino group, a heteroalicyclic ring.

2. The method of claim 1, wherein at least one of $R^1$ and $R^3$ is independently selected from the group consisting of H, $CH_3$, $CH(CH_3)_2$, $CH_2CH(CH_3)_2$, $CH(CH_3)CH_2CH_3$, $(CH_2)_2$—S—$CH_3$, $CH_2$—SH, $CH_2$—OH, CHOH—$CH_3$, $CH_2$-(3-indolyl), $CH_2$-phenyl, $(CH_2)_4$—$NH_2$, $(CH_2)_3$—NH—C(═NH)$NH_2$, $CH_2$-1H-imidazol-4-yl, $CH_2$-(p-hydroxy-phenyl), $CH_2$—C(O)$NH_2$, $(CH_2)_2$—C(O)$NH_2$, $CH_2$—COOH, and $(CH_2)_2$—COOH, or $R^1$ is $(CH_2)_3$ that forms together with the nitrogen of the adjacent backbone imino group a 5-membered heteroalicyclic ring.

3. The method of claim 1, wherein $R^2$ is selected from the group consisting of H, $CH_3$, $CH(CH_3)_2$, $CH_2CH(CH_3)_2$, $CH(CH_3)CH_2CH_3$, $(CH_2)_2$—S—$CH_3$, $CH_2$—SH, $CH_2$—OH, CHOH—$CH_3$, $CH_2$-(3-indolyl), $CH_2$-phenyl, $(CH_2)_4$—$NH_2$, $(CH_2)_3$—NH—C(═NH)$NH_2$, $CH_2$-1H-imidazol-4-yl, $CH_2$-(p-hydroxy-phenyl), $CH_2$—C(O)$NH_2$, $(CH_2)_2$—C(O)$NH_2$, $CH_2$—COOH, and $(CH_2)_2$—COOH.

4. The method of claim 1, wherein the reducing agent is samarium (II) iodide ($SmI_2$) solution.

5. The method of claim 4, wherein the reducing agent is $SmI_2$ solution in tetrahydrofuran (THF) or $SmI_2$ solution in trifluoroethanol (TFE).

6. The method of claim 1, wherein the organic acid is acetic acid, propionic acid, isobutyric acid or butyric acid.

7. The method of claim 1, wherein the intermediate compound has the following formula (4):

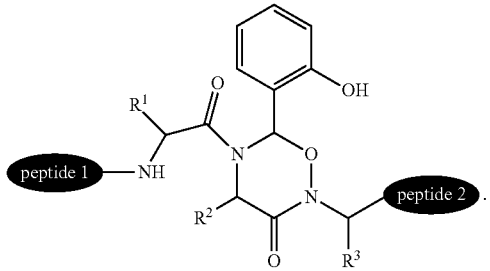
(4)

8. The method of claim 2, wherein at least one of $R^1$, $R^2$ and $R^3$ is independently selected from the group consisting of $CH_3$, $CH_2$-phenyl, $CH_2CH(CH_3)_2$, $CH(CH_3)_2$ and H.

9. The method of claim 2, wherein:
$R^1$ is $CH_3$ and $R^2$ is $CH_3$;
$R^1$ is $CH_3$ and $R^2$ is H;
$R^1$ is $CH_3$ and $R^2$ is $CH_2$-phenyl;
$R^1$ is $CH_3$ and $R^2$ is $CH_2CH(CH_3)_2$;
$R^1$ is $CH_2$-phenyl and $R_2$ is $CH_3$;
$R^1$ is $CH_2CH(CH_3)_2$ and $R^2$ is $CH_3$;
$R^1$ is $CH(CH_3)_2$ and $R^2$ is $CH_3$;
$R^1$ is $CH(CH_3)_2$ and $R^2$ is H;
$R^1$ is $CH_2CH(CH_3)_2$ and $R^2$ is $CH_2CH(CH_3)_2$; or
$R^1$ is $CH_2$-phenyl and $R^2$ is $CH_2CH(CH_3)_2$.

10. A method of preparing a cyclic peptide of formula (5)

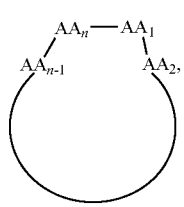
(5)

where $AA_n$ represents an amino acid at a $n^{th}$ position of the peptide, comprising:
reacting the C-terminal salicylaldehyde ester peptide of formula (1A)

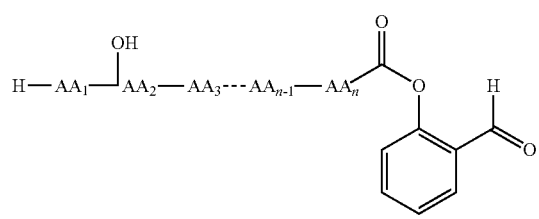
(1A)

in a pyridine/organic acid mixture, where " - - - " represents additional amino acids in the chain of the peptide; and
adding a reducing agent to form the cyclic peptide of formula (5).

11. The method of claim 10, wherein the reducing agent is $SmI_2$ solution.

12. The method of claim 10, wherein the reducing agent is $SmI_2$ solution in THF or $SmI_2$ solution in TFE.

13. The method of claim 10, wherein the organic acid is acetic acid, propionic acid, isobutyric acid or butyric acid.

14. A method of preparing a serinyl- or threonyl-containing cyclic peptide of formula (6)

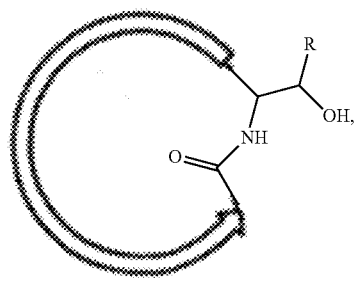
(6)

where the peptide contains serine (Ser) or threonine (Thr), comprising:
reacting the C-terminal Ser- or Thr-containing salicylaldehyde ester peptide of formula (1B)

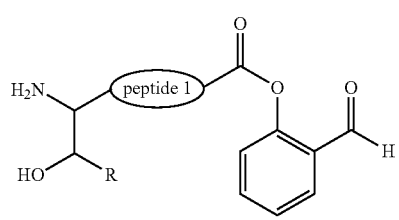
(1B)

in a pyridine/organic acid mixture; and
adding an acidic deprotecting agent to form the serinyl- or threonyl-containing cyclic peptide of formula (6),
wherein R is a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl, or a side chain of an amino acid.

15. The method of claim 14, wherein the acidic deprotecting agent to deprotect the oxazolidine ring is trifluoroacetic acid (TFA).

16. The method of claim 14, wherein the organic acid is acetic acid, propionic acid, isobutyric acid, or butyric acid.

17. A method of preparing a C-terminal salicylaldehyde ester peptide in solid phase, comprising:
(i) mixing 2-hydroxycinnamic acid and 4-methylbenzhydrylamine hydrochloride salt (MBHA) resin in the presence of benzotriazol-1-yl-oxytripyrrolidinophosphonium hexafluorophosphate (PyBOP) and a tertiary amine to form a 2-hydroxycinnamamide linker on the resin;
(ii) coupling a Boc-amino acid to the 2-hydroxycinnamamide linker-resin, followed by standard Boc solid phase peptide synthesis to form a peptidyl 2-hydroxycinnamamide phenolic ester on the resin, where Boc represents tert-butoxycarbonyl protecting group;

(iii) adding a cleavage agent to release the peptidyl 2-hydroxycinnamamide phenolic ester from the resin; and (iv) ozonizing the C=C bond of the peptidyl 2-hydroxycinnamamide phenolic ester to obtain the C-terminal salicylaldehyde ester peptide.

18. The method of claim 17, wherein the tertiary amine is diisopropylethylamine (DIEA).

19. The method of claim 17, wherein the cleavage agent is hydrofluoric acid or trifluoromethanesulfonic acid-trifluoroacetic acid mixture.

20. A method of preparing a polypeptide or protein of formula (7)

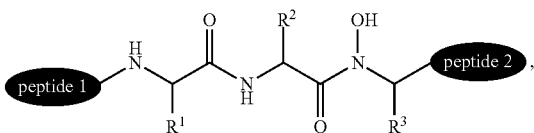
(7)

comprising reacting a compound of formula (4)

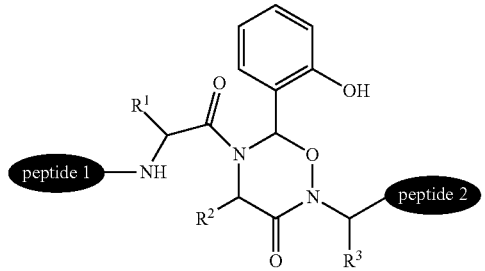
(4)

with trifluoroacetic acid (TFA), wherein each of $R^1$, $R^2$ and $R^3$ is independently selected from the group consisting of H, a substituted or unsubstituted $C_1$-$C_{10}$ alkyl, substituted or unsubstituted $C_2$-$C_{15}$ alkenyl, substituted or unsubstituted $C_2$-$C_{15}$ alkynyl, substituted or unsubstituted $C_3$-$C_{15}$ cycloalkyl, substituted or unsubstituted $C_3$-$C_{15}$ cycloalkenyl, substituted or unsubstituted $C_3$-$C_{15}$ heterocycloalkyl, substituted or unsubstituted $C_3$-$C_{15}$ heterocycloalkenyl, substituted or unsubstituted $C_6$-$C_{15}$ aryl, or substituted or unsubstituted $C_6$-$C_{15}$ heteroaryl, and a side chain of an amino acid.

* * * * *

UNITED STATES PATENT AND TRADEMARK OFFICE
CERTIFICATE OF CORRECTION

PATENT NO. : 9,453,044 B2
APPLICATION NO. : 14/376675
DATED : September 27, 2016
INVENTOR(S) : Chuan Fa Liu et al.

It is certified that error appears in the above-identified patent and that said Letters Patent is hereby corrected as shown below:

In the Claims

Column 48, Line 49:
"NH-C(-NH)NH$_2$, CH$_2$-11H-imidazol-4-yl, CH$_2$-(p-hydroxy-phenyl)," should read,
--NH-C(=NH)NH$_2$, CH$_2$-11H-imidazol-4-yl, CH$_2$-(p-hydroxy-phenyl),--.

Column 50, Lines 28-38:

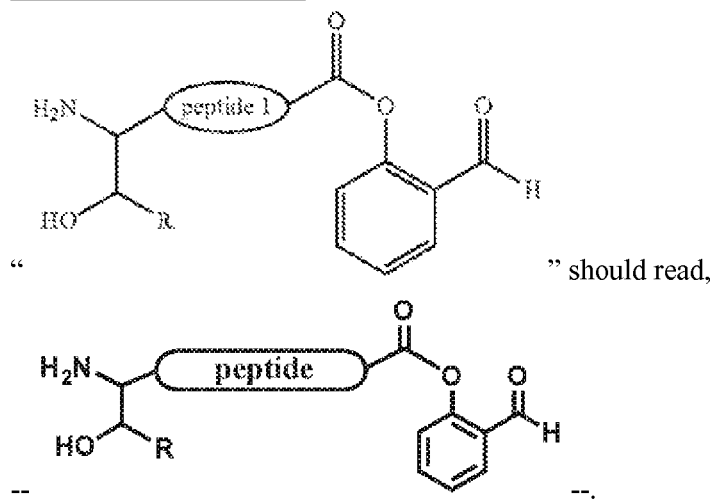

Signed and Sealed this
Eleventh Day of April, 2017

Michelle K. Lee
*Director of the United States Patent and Trademark Office*

SEQUENCE LISTING

```
<160> NUMBER OF SEQ ID NOS: 17

<210> SEQ ID NO 1
<211> LENGTH: 8
<212> TYPE: PRT
<213> ORGANISM: Artificial
<220> FEATURE:
<223> OTHER INFORMATION: Peptide substrate
<220> FEATURE:
<221> NAME/KEY: misc_feature
<222> LOCATION: (2)..(2)
<223> OTHER INFORMATION: X is N-hydroxy-Ala.
<220> FEATURE:
<221> NAME/KEY: amidation
<222> LOCATION: (8)..(8)
<223> OTHER INFORMATION: X is Ala-NH2.

<400> SEQUENCE: 1

Gly Xaa Gly Val Gly Leu Phe Xaa
1               5

<210> SEQ ID NO 2
<211> LENGTH: 9
<212> TYPE: PRT
<213> ORGANISM: Artificial
<220> FEATURE:
<223> OTHER INFORMATION: Peptide substrate
<220> FEATURE:
<221> NAME/KEY: misc_feature
<222> LOCATION: (1)..(1)
<223> OTHER INFORMATION: X is Fmoc-Ala.
<220> FEATURE:
<221> NAME/KEY: amidation
<222> LOCATION: (9)..(9)
<223> OTHER INFORMATION: X is Ala-NH2.
```

```
<400> SEQUENCE: 2

Xaa Gly Ala Gly Val Gly Leu Phe Xaa
1               5

<210> SEQ ID NO 3
<211> LENGTH: 5
<212> TYPE: PRT
<213> ORGANISM: Artificial
<220> FEATURE:
<223> OTHER INFORMATION: Peptide substrate
<220> FEATURE:
<221> NAME/KEY: acetylation
<222> LOCATION: (1)..(1)
<223> OTHER INFORMATION: X is Acetyl-Leu.
<220> FEATURE:
<221> NAME/KEY: misc_feature
<222> LOCATION: (5)..(5)
<223> OTHER INFORMATION: X is Gly-OPhCHO.

<400> SEQUENCE: 3

Xaa Gly Phe Ala Xaa
1               5

<210> SEQ ID NO 4
<211> LENGTH: 7
<212> TYPE: PRT
<213> ORGANISM: Artificial
<220> FEATURE:
<223> OTHER INFORMATION: Peptide substrate
<220> FEATURE:
<221> NAME/KEY: misc_feature
<222> LOCATION: (2)..(2)
<223> OTHER INFORMATION: X is N-hydroxy-Ala.
<220> FEATURE:
<221> NAME/KEY: amidation
<222> LOCATION: (7)..(7)
<223> OTHER INFORMATION: X is Gly-NH2.

<400> SEQUENCE: 4

Gly Xaa Gly Val Ser Ala Xaa
1               5

<210> SEQ ID NO 5
<211> LENGTH: 12
<212> TYPE: PRT
<213> ORGANISM: Artificial
<220> FEATURE:
<223> OTHER INFORMATION: Peptide substrate
<220> FEATURE:
<221> NAME/KEY: acetylation
<222> LOCATION: (1)..(1)
<223> OTHER INFORMATION: X is Acetyl-Leu.
<220> FEATURE:
<221> NAME/KEY: amidation
<222> LOCATION: (12)..(12)
<223> OTHER INFORMATION: X is Gly-NH2.

<400> SEQUENCE: 5

Xaa Gly Phe Ala Gly Gly Ala Gly Val Ser Ala Xaa
1               5                   10

<210> SEQ ID NO 6
<211> LENGTH: 13
<212> TYPE: PRT
<213> ORGANISM: Artificial
<220> FEATURE:
<223> OTHER INFORMATION: Peptide substrate
<220> FEATURE:
<221> NAME/KEY: acetylation
<222> LOCATION: (1)..(1)
<223> OTHER INFORMATION: X is Acetyl-Leu.
```

```
<220> FEATURE:
<221> NAME/KEY: amidation
<222> LOCATION: (13)..(13)
<223> OTHER INFORMATION: X is Ala-NH2.

<400> SEQUENCE: 6

Xaa Gly Phe Ala Gly Gly Ala Gly Val Gly Leu Phe Xaa
1               5                   10

<210> SEQ ID NO 7
<211> LENGTH: 8
<212> TYPE: PRT
<213> ORGANISM: Artificial
<220> FEATURE:
<223> OTHER INFORMATION: Peptide substrate
<220> FEATURE:
<221> NAME/KEY: misc_feature
<222> LOCATION: (2)..(2)
<223> OTHER INFORMATION: X is N-hydroxy-Ala.
<220> FEATURE:
<221> NAME/KEY: amidation
<222> LOCATION: (8)..(8)
<223> OTHER INFORMATION: X is Ala-NH2.

<400> SEQUENCE: 7

Phe Xaa Gly Val Gly Leu Phe Xaa
1               5

<210> SEQ ID NO 8
<211> LENGTH: 13
<212> TYPE: PRT
<213> ORGANISM: Artificial
<220> FEATURE:
<223> OTHER INFORMATION: Peptide substrate
<220> FEATURE:
<221> NAME/KEY: acetylation
<222> LOCATION: (1)..(1)
<223> OTHER INFORMATION: X is Acetyl-Leu.
<220> FEATURE:
<221> NAME/KEY: amidation
<222> LOCATION: (13)..(13)
<223> OTHER INFORMATION: X is Ala-NH2.

<400> SEQUENCE: 8

Xaa Gly Phe Ala Gly Phe Ala Gly Val Gly Leu Phe Xaa
1               5                   10

<210> SEQ ID NO 9
<211> LENGTH: 7
<212> TYPE: PRT
<213> ORGANISM: Artificial
<220> FEATURE:
<223> OTHER INFORMATION: Peptide substrate
<220> FEATURE:
<221> NAME/KEY: misc_feature
<222> LOCATION: (2)..(2)
<223> OTHER INFORMATION: X is N-hydroxy-Ala.
<220> FEATURE:
<221> NAME/KEY: amidation
<222> LOCATION: (7)..(7)
<223> OTHER INFORMATION: X is Gly-NH2.

<400> SEQUENCE: 9

Leu Xaa Gly Val Ser Ala Xaa
1               5

<210> SEQ ID NO 10
<211> LENGTH: 12
<212> TYPE: PRT
<213> ORGANISM: Artificial
<220> FEATURE:
```

```
<223> OTHER INFORMATION: Peptide substrate
<220> FEATURE:
<221> NAME/KEY: acetylation
<222> LOCATION: (1)..(1)
<223> OTHER INFORMATION: X is Acetyl-Leu.
<220> FEATURE:
<221> NAME/KEY: amidation
<222> LOCATION: (12)..(12)
<223> OTHER INFORMATION: X is Gly-NH2.

<400> SEQUENCE: 10

Xaa Gly Phe Ala Gly Leu Ala Gly Val Ser Ala Xaa
1               5                   10

<210> SEQ ID NO 11
<211> LENGTH: 6
<212> TYPE: PRT
<213> ORGANISM: Artificial
<220> FEATURE:
<223> OTHER INFORMATION: Peptide

<400> SEQUENCE: 11

Ser Gly Lys Ala Phe Leu
1               5

<210> SEQ ID NO 12
<211> LENGTH: 5
<212> TYPE: PRT
<213> ORGANISM: Artificial
<220> FEATURE:
<223> OTHER INFORMATION: Peptide

<400> SEQUENCE: 12

Ser Phe Leu Phe Ala
1               5

<210> SEQ ID NO 13
<211> LENGTH: 8
<212> TYPE: PRT
<213> ORGANISM: Artificial
<220> FEATURE:
<223> OTHER INFORMATION: Peptide

<400> SEQUENCE: 13

Thr Gly Leu Phe Gly Phe Ala Gly
1               5

<210> SEQ ID NO 14
<211> LENGTH: 8
<212> TYPE: PRT
<213> ORGANISM: Artificial
<220> FEATURE:
<223> OTHER INFORMATION: Peptide

<400> SEQUENCE: 14

Ser Gly Leu Phe Gly Phe Ala Gly
1               5

<210> SEQ ID NO 15
<211> LENGTH: 8
<212> TYPE: PRT
<213> ORGANISM: Artificial
<220> FEATURE:
<223> OTHER INFORMATION: Peptide

<400> SEQUENCE: 15

Ser Gly Leu Tyr Gly Phe Ala Gly
1               5
```

```
<210> SEQ ID NO 16
<211> LENGTH: 4
<212> TYPE: PRT
<213> ORGANISM: Artificial
<220> FEATURE:
<223> OTHER INFORMATION: Peptide

<400> SEQUENCE: 16

Ser Leu Ser Leu
1

<210> SEQ ID NO 17
<211> LENGTH: 7
<212> TYPE: PRT
<213> ORGANISM: Artificial
<220> FEATURE:
<223> OTHER INFORMATION: Peptide

<400> SEQUENCE: 17

Thr Phe Phe Gly Phe Phe Gly
1               5
```